(12) United States Patent
Province et al.

(10) Patent No.: US 7,660,629 B2
(45) Date of Patent: *Feb. 9, 2010

(54) DEVICE AND METHOD FOR PREVENTING THE ACCELERATION OF CARDIAC ARRHYTHMIAS

(75) Inventors: Rose Province, San Jose, CA (US); Timothy A. Fayram, Gilroy, CA (US)

(73) Assignee: Pacesetter, Inc., Sylmar, CA (US)

( * ) Notice: Subject to any disclaimer, the term of this patent is extended or adjusted under 35 U.S.C. 154(b) by 623 days.

This patent is subject to a terminal disclaimer.

(21) Appl. No.: 11/564,725

(22) Filed: Nov. 29, 2006

(65) Prior Publication Data

US 2007/0088395 A1    Apr. 19, 2007

Related U.S. Application Data

(63) Continuation of application No. 10/901,403, filed on Jul. 27, 2004, now Pat. No. 7,181,276.

(51) Int. Cl.
*A61N 1/38* (2006.01)

(52) U.S. Cl. .................................... 607/7; 607/4; 607/5

(58) Field of Classification Search ...................... 607/4, 607/5, 7, 11, 14, 15, 63
See application file for complete search history.

(56) References Cited

U.S. PATENT DOCUMENTS

| 4,712,555 A | 12/1987 | Thomander et al. |
|---|---|---|
| 4,788,980 A | 12/1988 | Mann et al. |
| 4,940,052 A | 7/1990 | Mann et al. |
| 4,944,298 A | 7/1990 | Sholder |
| 4,996,984 A | 3/1991 | Sweeney |
| 4,998,974 A | 3/1991 | Aker |
| 4,998,975 A | 3/1991 | Cohen et al. |
| 5,183,040 A | 2/1993 | Nappholz et al. |
| 5,184,616 A | 2/1993 | Weiss |
| 5,222,480 A | 6/1993 | Couche et al. |
| 5,224,475 A | 7/1993 | Berg et al. |
| 5,318,591 A | 6/1994 | Cause, III et al. |
| 5,344,430 A | 9/1994 | Berg et al. |

(Continued)

FOREIGN PATENT DOCUMENTS

EP    0641573 B1    7/2001

(Continued)

OTHER PUBLICATIONS

Bardy, Gust H. MD, et al., "A Prospective Randomized Repeat-Crossover Comparison of Antitachycardia Pacing With Low-Energy Cardioversion," Circulation 1993; 87(6): 889-1896.

(Continued)

*Primary Examiner*—Carl H Layno
*Assistant Examiner*—Yun Haeng Lee

(57) ABSTRACT

An exemplary method includes detecting ventricular fibrillation, delivering a low voltage cardiac stimulus, determining whether the low voltage cardiac stimulus terminated the ventricular fibrillation, and delivering a higher voltage cardiac stimulus if the low voltage cardiac stimulus did not terminate the ventricular fibrillation. In one example, the delivering the low voltage cardiac stimulus occurs within approximately 10 event intervals from the detected onset of ventricular fibrillation; otherwise, delivery of an appropriate higher voltage cardiac stimulus occurs. Other exemplary methods, devices, systems, etc., are also disclosed.

20 Claims, 14 Drawing Sheets

U.S. PATENT DOCUMENTS

| | | | |
|---|---|---|---|
| 5,466,254 | A | 11/1995 | Helland |
| 5,476,483 | A | 12/1995 | Bornzin et al. |
| 5,534,019 | A | 7/1996 | Paspa |
| 5,578,062 | A | 11/1996 | Alt et al. |
| 5,620,469 | A | 4/1997 | Kroll |
| 5,620,477 | A | 4/1997 | Pless et al. |
| 5,709,710 | A | 1/1998 | Armstrong |
| 5,853,426 | A | 12/1998 | Shieh |
| 5,913,887 | A | 6/1999 | Michel |
| 5,978,705 | A | 11/1999 | KenKnight et al. |
| 6,041,256 | A | 3/2000 | Michel |
| 6,134,470 | A | 10/2000 | Hartlaub |
| 6,167,305 | A | 12/2000 | Cammilli et al. |
| 6,314,323 | B1 | 11/2001 | Ekwall |
| 6,431,173 | B1 | 8/2002 | Hoffmann |
| 6,438,418 | B1 | 8/2002 | Swerdlow et al. |
| 6,456,876 | B1 | 9/2002 | Kroll |
| 6,477,417 | B1 | 11/2002 | Levine |
| 6,539,256 | B1 | 3/2003 | KenKnight et al. |
| 6,690,971 | B2 | 2/2004 | Schauerte et al. |
| 6,711,442 | B1 | 3/2004 | Swerdlow et al. |
| 7,072,711 | B2 | 7/2006 | Girouard et al. |
| 2002/0042631 | A1 | 4/2002 | Michel |
| 2002/0103507 | A1 | 8/2002 | Helland |
| 2003/0060724 | A1 | 3/2003 | Thiagarajan et al. |
| 2005/0049516 | A1 | 3/2005 | Ideker |
| 2005/0256544 | A1 | 11/2005 | Thompson |

FOREIGN PATENT DOCUMENTS

| | | |
|---|---|---|
| WO | 9840122 | 9/1998 |
| WO | 0234123 A2 | 5/2002 |
| WO | 03071945 A1 | 9/2003 |

OTHER PUBLICATIONS

Levy, Samuel MD et al., "Low-Energy Cardioversion of Spontaneous Atrial Fibrillation—Immediate and Long-Term Results," Circulation 1997; 96(1): 253-259.

Sinha, Sitabhra et al., "Critical Role of Inhomogeneities in Pacing Termination of Cardiac Reentry," CHAOS 2002; 12(3): 893-902.

Weiss, James N. et al., "Ventricular Fibrillation—How Do We Stop the Waves From Breaking?" Circ. Res. 2000; 87: 1103-1107.

Banville, Isabelle Ph.D. et al., "Effect of Action Potential Duration and Conduction Velocity Restitution and Their Spatial Dispersion on Alternans and the Stability of Arrhythmias," J Cardiovasc Electrophysiol. Nov. 2002;13:1141-1149.

Can, Ilknur et al., "Physiological Mechanisms Influencing Cardiac Repolarization and QT Interval," Cardiac Electrophysiology Review. 2002;6:278-281.

Hashimoto, Hisakuni Ph.D. et al., "Effects of the Ventricular Premature Beat on the Alternation of the Repolarization Phase in Ischemic Myocardium during Acute Coronary Occlusion in Dogs," J. Electrophysiology. 1984;17(3):229-238.

Hashimoto, H. et al., "Evidence for a link between mechanical and electrical alternans in acutely ischaemic myocardium of anaesthetized dogs," Acta Physiol Scan. 1991;141:63-70.

Hashimoto, Hisakuni Ph.D. et al., "Potentiating Effects of a Ventricular Premature Beat on the Alternation of the ST-T Complex of Epicardial Electrograms and the Incidence of Ventricular Arrhythmias during Acute Coronary Occlusion in Dogs," J. Electrophysiology. 1984;17(3):289-302.

Konta, Tsuyoshi MD et al., "Significance of Discordant ST Alternans in Ventricular Fibrillation," Circulation. 1990;82:2185-2189.

Murphy, C.F. et al., "Regional electromechanical alternans in anesthetized pig hearts: modulation by mechanoelectric feedback," The American Physiological Society. 1994:H1726-H1735.

Nearing, Bruce D. et al., "Progressive Increases in Complexity of T-Wave Oscillations Herald Ischemia-Induced Ventricular Fibrillation," Circ Res. 2002;91:727-732.

Pastore, Joseph M. et al., "Role of Structural Barriers in the Mechanism of Alternans-Induced Reentry," Circ Res. 2000;87:1157-1163.

Pastore, Joseph M. MS et al., "Mechanism Linking T-Wave Alternans to the Genesis of Cardiac Fibrillation," Circulation. 1999;99:1385-1394.

Qu, Zhilin Ph.D. et al., "Mechanisms of Discordant Alternans and Induction of Reentry in Simulated Cardiac Tissue," Circulation. 2000;102:1664-1670.

Rubenstein, Donald S. MD et al., "Premature Beats Elicit a Phase Reversal of Mechanoelectrical Alternans in Cat Ventricular Myocytes: A Possible Mechanism for Reentrant Arrhythmias," Circulation. 1995;91:201-214.

Tachibana, Hidetada et al., "Discordant S-T alternans contributes to formation of reentry: a possible mechanism of reperfusion arrhythmia," Am J Physiol Heart Circ Physiol. 1998;275(1):H116-H121.

Watanabe, Mari A. MD et al., "Mechanisms for Discordant Alternans," J Cardiovasc Electrophysiol. Feb. 2001;12:196-206.

NonFinal Office Action, mailed Nov. 29, 2006: Related U.S. Appl. No. 10/901,480.

Final Office Action, mailed Jun. 5, 2007: Related U.S. Appl. No. 10/901,480.

Notice of Allowance, mailed Aug. 14, 2007: Related U.S. Appl. No. 10/901,480.

NonFinal Office Action, mailed Apr. 21, 2006: Related U.S. Appl. No. 10/901,403.

Notice of Allowance, mailed Aug. 30, 2006: Related U.S. Appl. No. 10/901,403.

NonFinal Office Action, mailed Jul. 20, 2006: Related U.S. Appl. No. 10/848,853.

Notice of Allowance, mailed Mar. 26, 2007: Related U.S. Appl. No. 10/848,853.

NonFinal Office Action, mailed Aug. 8, 2006: Related U.S. Appl. No. 10/901,421.

NonFinal Office Action, mailed Jan. 19, 2007: Related U.S. Appl. No. 10/901,421.

Advisory Action, mailed Apr. 3, 2007: Related U.S. Appl. No. 10/901,421.

NonFinal Office Action, mailed May 23, 2007: Related U.S. Appl. No. 10/901,421.

Final Office Action, mailed Oct. 25, 2007: Related U.S. Appl. No. 10/901,421.

EXEMPLARY CARDIAC RHYTHM

EXEMPLARY SCHEMES 700

DISCHARGE C_1 AND C_2
CHARGE C_1 AND C_2
710

DISCHARGE C_1 AND C_2
720

DISCHARGE C_1
CHARGE C_1 AND C_2
730

DISCHARGE C_1
CHARGE C_2
740

EXEMPLARY CIRCUIT AND PERFORMANCE ⟵ 900

EXEMPLARY H-BRIDGE ⟵ 910

EXEMPLARY DISCHARGE ⟵ 920

DEVICE AND METHOD FOR PREVENTING THE ACCELERATION OF CARDIAC ARRHYTHMIAS

RELATED APPLICATIONS

This application is a continuation of U.S. patent application Ser. No. 10/901,403, filed Jul. 27, 2004, now U.S Pat. No. 7,181,276. This application is related to U.S. patent applications: 1) Ser. No. 10/901,480, filed Jul. 27, 2004, now U.S. Pat. No. 7,308,305, entitled "Optimally Timed Early Shock Defibrillation" to Province and Kroll; 2) Ser. No. 10/901,421, filed Jul. 27, 2004, entitled "Optimized Pathways to Early Shock Defibrillation" to Province and Kroll; and 3) Ser. No. 10/848,853, filed May 18, 2004, now U.S. Pat. No. 7,225,014, entitled "Anti-Arrhythmia Therapy Based on Spatial and/or Temporal Information" to Province. All applications are incorporated herein by reference.

TECHNICAL FIELD

Exemplary methods, devices, systems, etc., presented herein generally relate to cardiac pacing and/or stimulation therapy. Various exemplary methods, devices, systems, etc., aim to deliver anti-arrhythmia stimulation at energies less than those conventionally used for defibrillation.

BACKGROUND

Ventricular fibrillation is a potentially life-threatening cardiac condition. Most conventional defibrillation devices, whether external or implantable, treat ventricular fibrillation with a cardiac stimulus of quite high energy. For example, external devices typically use an energy level in excess of approximately 200 joules and implantable devices typically use an energy level in excess of 10 joules. Such stimuli can be quite painful when delivered to a conscious patient. For an implantable device, such stimuli can also greatly impact the device's limited power supply. Further, while an implantable device requires lesser energy level stimulus for defibrillation compared to an external device, the consequences on size, weight and/or shape of an implantable device capable of producing a 10 joules stimulus is significant.

Recent studies using mathematical models, non-human animals and/or external devices have shown that at the onset of ventricular fibrillation, the number of reentry wavefronts may be low, for example, on the order of 1 or 2, similar to a monomorphic tachycardia. During subsequent activations, the fast activation rate of reentry wavefronts compared to sinus rhythm wavefronts causes an increase in electrical heterogeneity of the cardiac tissue, which, in turn, can cause an increasing number of wavefronts through wavefront breakup. Indeed, wavefront breakup may play an important role in the acceleration of an arrhythmia into a stable ventricular fibrillation. The time that is takes for such a transition to occur may be expected to vary, for example, from patient to patient, and experimentally from model to model.

As described herein, various exemplary methods, systems and/or devices aim to detect ventricular fibrillation or precursors thereof at an early stage, for example, prior to stabilization. Based on such detection, such exemplary methods, systems and/or devices may deliver one or more stimuli to terminate, disrupt or otherwise convert physiological processes related to wavefront breakup.

SUMMARY

An exemplary method includes detecting ventricular fibrillation, delivering a low voltage cardiac stimulus, determining whether the low voltage cardiac stimulus terminated the ventricular fibrillation, and delivering a higher voltage cardiac stimulus if the low voltage cardiac stimulus did not terminate the ventricular fibrillation. In one example, the delivering the low voltage cardiac stimulus occurs within approximately 10 intervals from the detected onset of ventricular fibrillation; otherwise, delivery of an appropriate higher voltage cardiac stimulus occurs. Such a higher voltage stimulus may follow detection and a charging delay (e.g., approximately 7 s to approximately 10 s) when required. Other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate and/or shock a patient's heart.

Figure 1:
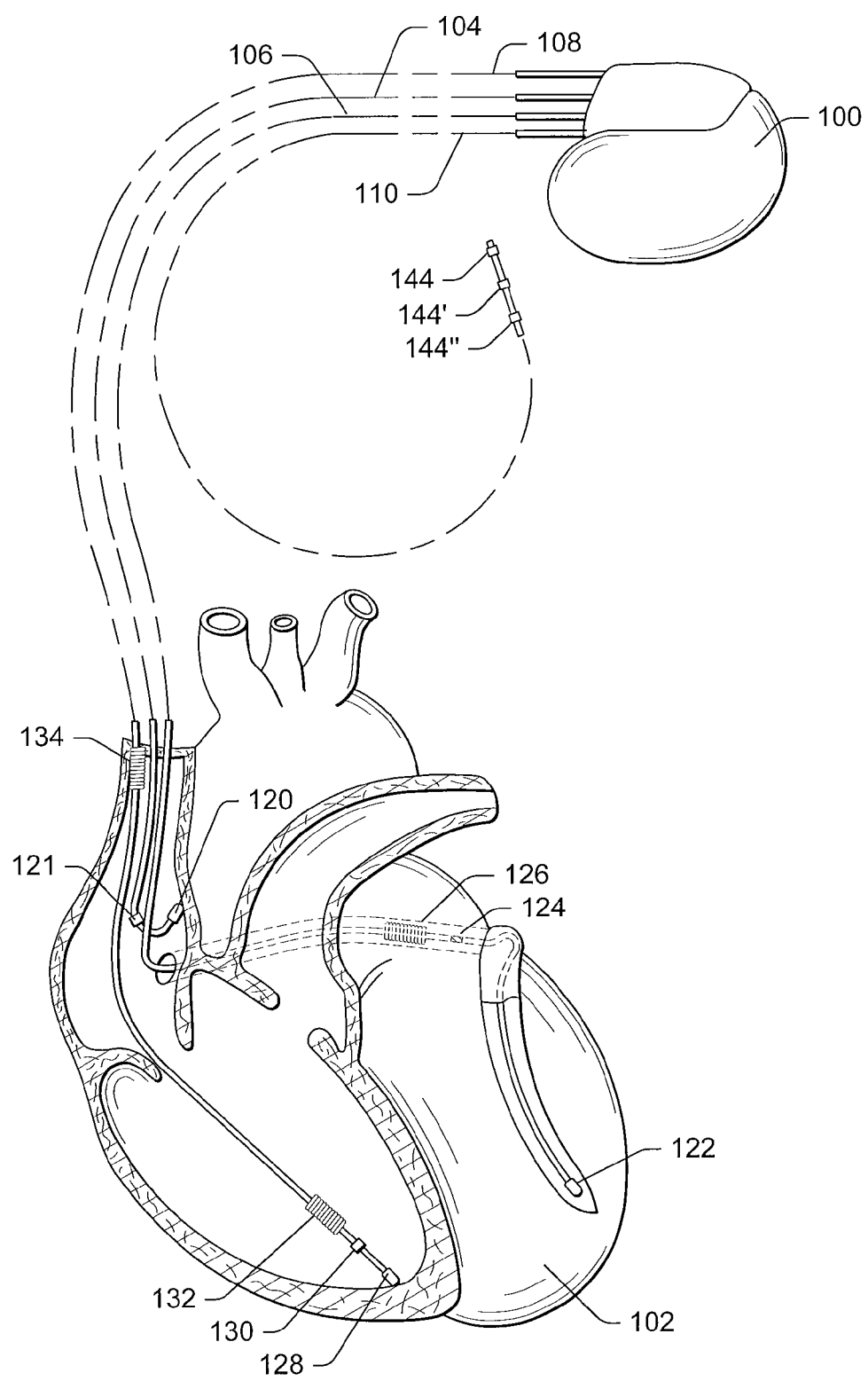
FIG. 1 is a simplified diagram illustrating an exemplary implantable stimulation device in electrical communication with at least three leads implanted into a patient's heart and at least one other lead for sensing and/or delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves and/or non-cardiac tissue. In addition, the device 100 includes a fourth lead 110 having, in this implementation, three electrodes 144, 144', 144" suitable for stimulation and/or detection of physiologic signals that may be used by the implanted system to modify therapy parameters. This lead may be positioned in and/or near a patient's heart or near a tissue within a patient's body and remote from the heart.

The right atrial lead 104, as the name implies, is positioned in and/or passes through a patient's right atrium. The right atrial lead 104 optionally senses atrial cardiac signals and/or provides right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation and/or sensing.

To sense atrial cardiac signals, ventricular cardiac signals and/or to provide cardiac therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular stimulation therapy using, for example, at least a left ventricular tip electrode 122, left atrial stimulation therapy using at least a left atrial ring electrode 124, and stimulation therapy using at least a left atrial coil electrode 126. Coil electrodes are often used for shock therapy. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference. The coronary sinus lead 106 may further include bifurcations or legs. For example, an exemplary coronary sinus lead includes stimulation electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include an electrode positioned on a bifurcation or leg of the lead.

Figure 2:
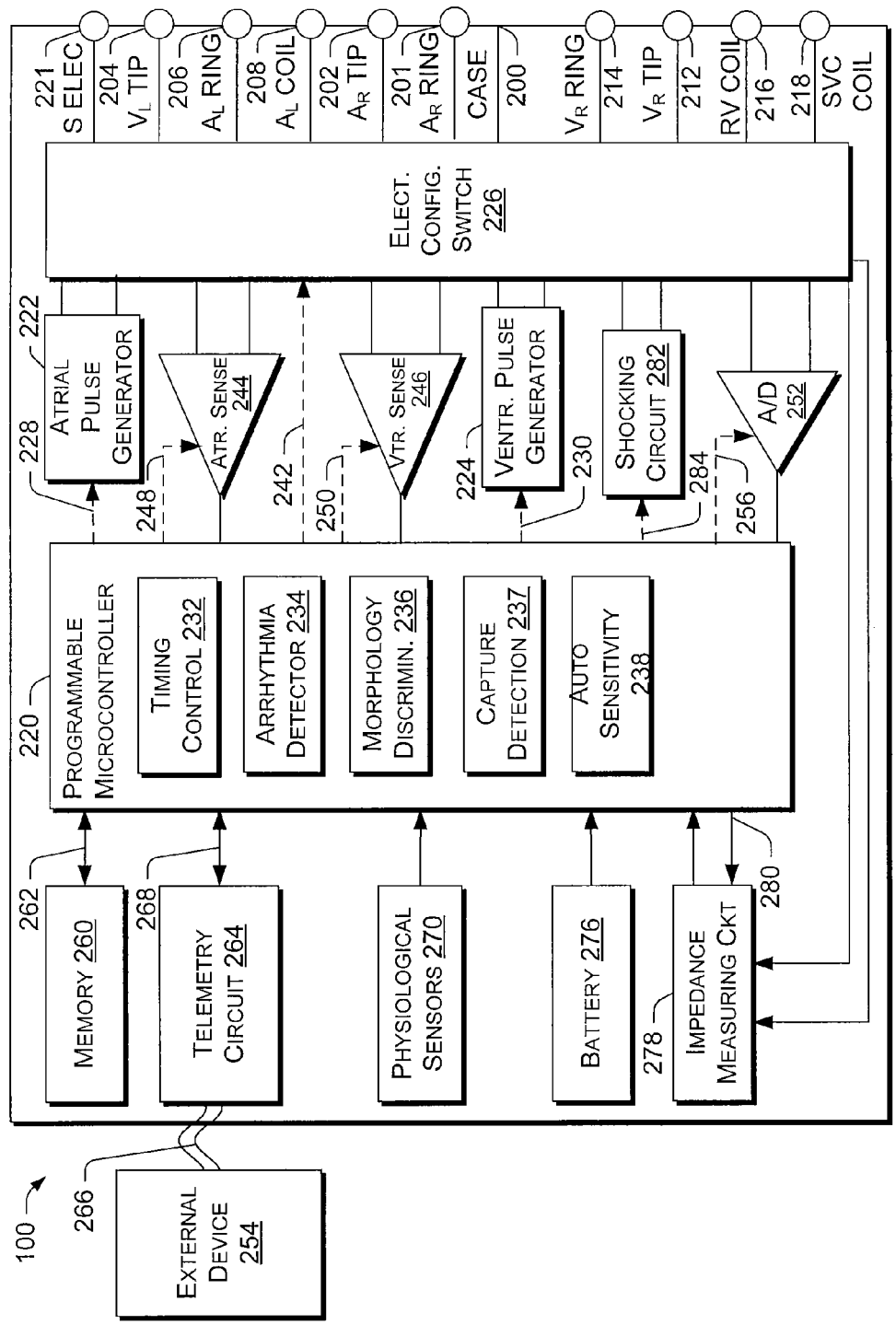
FIG. 2 is a functional block diagram of an exemplary implantable stimulation device illustrating basic elements that are configured to provide cardioversion, defibrillation, pacing stimulation and/or autonomic nerve stimulation or other tissue and/or nerve stimulation. The implantable stimulation device is further configured to sense information and administer stimulation pulses responsive to such information.

FIG. 2 shows an exemplary, simplified block diagram depicting various components of the stimulation device 100. The stimulation device 100 can be capable of treating both fast and slow arrhythmias with stimulation therapy, including cardioversion, defibrillation, and pacing stimulation. The stimulation device 100 may also deliver therapy according to various mechanisms disclosed herein. While a particular multi-chamber device is shown, it is to be appreciated and understood that this is done for illustration purposes only. Thus, the mechanisms (e.g., methods, devices, systems, etc.) described below can be implemented in connection with any suitably configured or configurable stimulation device. Accordingly, given the description herein, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, shock stimulation, etc.

Housing 200 for the stimulation device 100 is often referred to as the "can", "case" or "case electrode", and may be programmably selected to act as a return electrode for all "unipolar" modes (e.g., unipolar electrode configurations). Housing 200 may further be used as a return electrode alone or in combination with one or more of the coil electrodes 126, 132 and 134 for shocking purposes. As described herein other electrodes (coil or other) are optionally used to deliver shock therapy. Housing 200 further includes a connector (not shown) having a plurality of terminals 201, 202, 204, 206, 208, 212, 214, 216, 217, 218, 221 (shown schematically and, for convenience, the names of the electrodes to which they are connected are shown next to the terminals).

To achieve right atrial sensing and/or stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing and/or stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a stimulation terminal S ELEC 221). The stimulation terminal S ELEC 221 may also allow for sensing per appropriate connections or switching.

To support right chamber sensing and/or stimulation, the connector further includes a right ventricular tip terminal ($V_R$ TIP) 212, a right ventricular ring terminal ($V_R$ RING) 214, a right ventricular shocking terminal (RV COIL) 216, a left ventricle shocking terminal (LV COIL) 217 (e.g., for an optional LV coil or other electrode), and a superior vena cava shocking terminal (SVC COIL) 218, which are adapted for connection to the right ventricular tip electrode 128, right ventricular ring electrode 130, the RV coil electrode 132, an optional LV coil electrode (not shown in FIG. 1), and the SVC coil electrode 134, respectively. Connection to suitable autonomic nerve stimulation electrodes is also possible via these and/or other terminals (e.g., via the stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to nerves, other tissue, etc.) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 can be utilized by the stimulation device 100 for determining desirable times to administer various therapies. The arrhythmia detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. The arrhythmia detector 234 may receive such signals or processed signals and determine whether an arrhythmic condition exists, is likely to exist and/or is imminent. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary arrhythmia detector module 234 optionally uses timing intervals between sensed events (e.g., P-waves, R-waves, and depolarization signals associated with fibrillation which are sometimes referred to as "F-waves" or "Fib-waves") to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) to determine a type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). The exemplary arrhythmia detector 234 may also receive information from a physiologic sensor(s) 270, which may include a hemodynamic sensor, for example, as described below.

Detection techniques for heart condition that may be suitable for use with various exemplary methods, devices, systems, etc., disclosed herein include those of U.S. patent application Ser. No. 10/848,853, entitled "Anti-arrhythmia Therapy Based on Spatial and/or Temporal Information" to Province; and International PCT Application Serial No. PCT/SE03/00338 (WO 03/071945 A1), entitled "Medical Device" to Noren, which is incorporated by reference herein.

Similar rules can be applied to the atrial channel to determine if there is an atrial tachyarrhythmia or atrial fibrillation with appropriate classification and intervention. Such a module is optionally suitable for performing various exemplary methods described herein. For example, such a module optionally allows for analyses related to action potentials (e.g., MAPs, T waves, etc.) and characteristics thereof (e.g., alternans, activation times, repolarization times, derivatives, etc.).

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

As already mentioned, the stimulation device 100 can further include one or more physiologic sensor(s) 270. A commonly used physiologic sensor is a "rate-responsive" sensor that is typically used to adjust pacing stimulation rate according to the exercise state of the patient. However, the physiological sensor(s) 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor(s) 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensor(s) 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock or other stimulation pulse, for example, according to various exemplary methods, devices, systems, etc., described below. The battery 276 also desirably has a predictable discharge characteristic so that elective replacement time can be determined a priori or detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it may detect occurrence of an arrhythmia, and automatically apply an appropriate therapy to the heart aimed at terminating the detected arrhythmia and converting the heart back to a normal sinus rhythm. To this end, the microcontroller 220 further controls a shocking circuit 282 by way of a control signal 284. The shocking circuit 282 is presented as an example herein as other exemplary circuits are discussed below for charging and/or discharging stored charge.

In this example, the shocking circuit 282 can generate shocking or stimulation pulses of low (e.g., up to approximately 0.5 J), moderate (e.g., approximately 0.5 J to approximately 10 J), or high energy (e.g., approximately 11 J to approximately 40 J), as controlled by the microcontroller 220. The aforementioned ranges are representative of conventional ranges and various ranges are discussed further below wherein "low voltage" or "low energy" shocks may extend into the lower end of the aforementioned moderate energy range.

Various other mechanisms are described herein whereby an early shock may be delivered in response to an arrhythmic condition or a condition indicative of an arrhythmia. Such early shock mechanisms typically delivery a shock at an energy from approximately 0.1 J to approximately 5.0 J. In some examples, leading edge voltages for such early shocks range from approximately 50 V to approximately 300 V.

In general, shocking pulses are applied to the patient's heart 102 through at least two electrodes, and as shown in this embodiment, selected from the left atrial coil electrode 126, the RV coil electrode 132, and/or the SVC coil electrode 134.

As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Conventional cardioversion level shocks are generally considered to be of low to moderate energy level and synchronized with an R wave and/or pertaining to the treatment of tachycardia. In tiered therapy, a "low energy" or "low level" cardioversion tier is normally considered a first-line treatment for ventricular tachycardia (e.g., rates of over approximately 180 bpm). In conventional cardioversion therapy, synchronous QRS complex or R wave delivery aims to avoid delivery of energy during a vulnerable period of the T wave, which may initiate or accelerate transition to ventricular fibrillation.

Defibrillation shocks are generally of a moderate to a high energy level (e.g., corresponding to thresholds in the range of approximately 5 J to approximately 40 J) and a first-line treatment for ventricular fibrillation. If any recognizable QRS complex or R wave exists, or if atrial pacing is present, a defibrillation shock may be delivered synchronously. Accordingly, the microcontroller 220 is capable of controlling the synchronous or asynchronous delivery of the shocking pulses.

Cardiac Rhythms

Figure 3:
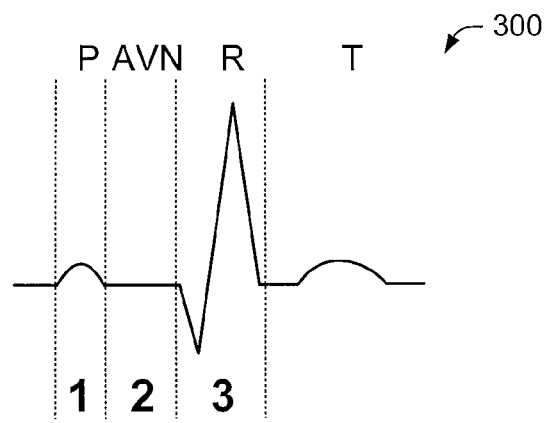
FIG. 3 is an approximate anatomical diagram of a heart and a waveform or ECG.
Figure 3:
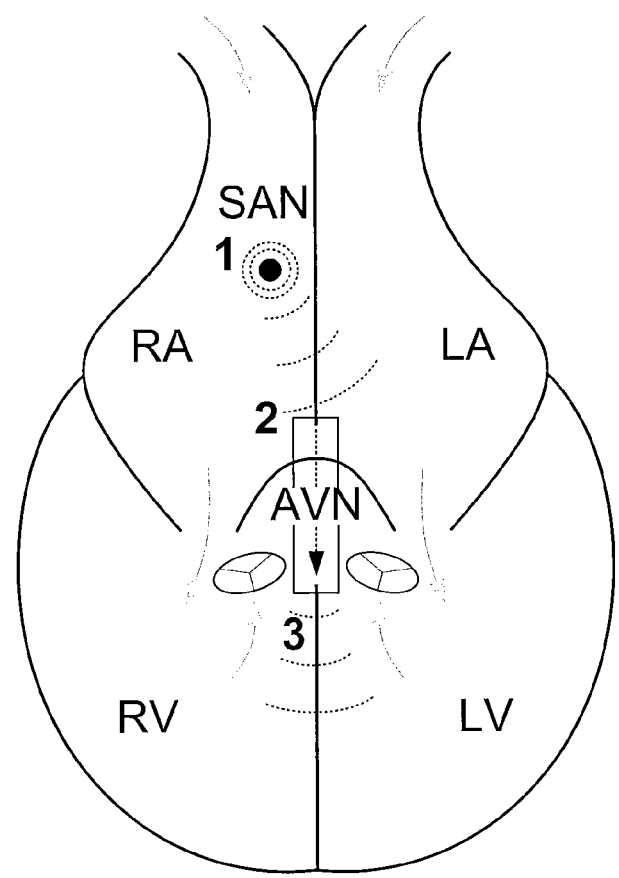

FIG. 3 shows an approximate anatomical diagram of a heart and an intrinsic waveform 300. Electrical activation propagating through a normal heart is labeled as follows: 1, associated with the sinoatrial node (SAN) and the atria; 2, associated with the atrioventricular node and/or atrioventricular bundle (AVN); and 3, associated with the ventricles. In a normal heart, cells of the SAN (1) spontaneously depolarize and thereby initiate an action potential (shown as dashed lines emanating from the SAN). This action potential propagates rapidly through the atria (which contract), slowly through the AVN (2) and then to the ventricles (3), which causes ventricular contraction. Thus, in a normal heart, ventricular rhythm relies on conduction of action potentials through the AV node and AV bundle (collectively referred to as the AV node or AVN).

An ECG of normal heart activity (e.g., polarization, depolarization, repolarization, etc.) typically shows atrial depolarization as a "P wave", ventricular depolarization as an "R wave", or QRS complex and ventricular repolarization as a T wave. The time span between a P wave and an R wave typically depends on AVN conduction and/or heart rate (e.g., rate of SAN). An ECG may also allow for determination of a QT interval, for example, measured from onset of a QRS complex to the end of ventricular repolarization (e.g., end of T wave). Yet further, an ECG may allow for determination of a ST interval, for example, measured from the end of a QRS complex to the end of a ventricular repolarization.

Ventricular Arrhythmias

Ventricular arrhythmia is a leading cause of sudden cardiac death. Detection of ventricular arrhythmia and/or precursors thereto can help in prevention of such deaths. The aforementioned exemplary implantable cardiac device 100 includes an ability to detect arrhythmia and/or precursors thereto and to respond to such detection. One particular response includes delivery of one or more stimuli to the heart. In general, such stimuli are referred to herein as "low voltage" stimuli or shocks as opposed to high voltage stimuli or shocks commonly associated with defibrillation.

Ventricular arrhythmias often involve reentry wavefronts or circuits that travel around poorly conducting or unresponsive cardiac scar tissue or that travel in a wholly functional myocardial region. Spatial information may help determine locations of such reentry circuits (e.g., their spatio-temporal characteristics). Some studies of pacing to terminate ventricular arrhythmias suggest pacing or delivering stimulation at a site wherein the position of the site is based on location of a reentry circuit. Various studies suggest pacing or delivering at a site proximate to the reentry circuit while others suggest pacing or delivering at a site removed from the reentry circuit. Of course, sometimes pacing or delivering is limited to a single site; consider, for example, an implantable cardiac device having a single lead with a pacing electrode positioned in a patient's right ventricle. In such instances, spatial and/or temporal information pertaining to a reentry circuit may prove beneficial, for example, in determining a pacing time and/or pacing amplitude, frequency, etc. As described herein, such information optionally includes information regarding homogeneity or heterogeneity of a reentry circuit. Further, characteristics of a reentry circuit optionally include information regarding ischemia, conduction velocity, etc.

Various factors may affect successful termination of a ventricular arrhythmia. Such factors include, but are not limited to, arrhythmia rate (e.g., path length and conduction velocity), refractory period at a pacing or stimulation site and/or in a reentry circuit, conduction path from pacing or stimulation site to a reentry circuit (e.g., including conduction velocity, conduction time, etc.), reentry circuit gap characteristics. See, e.g., Sinha, et al., "Critical role of inhomogeneities in pacing termination of cardiac reentry", *CHAOS,* 12(3): 893-902 (2002).

Figure 4:
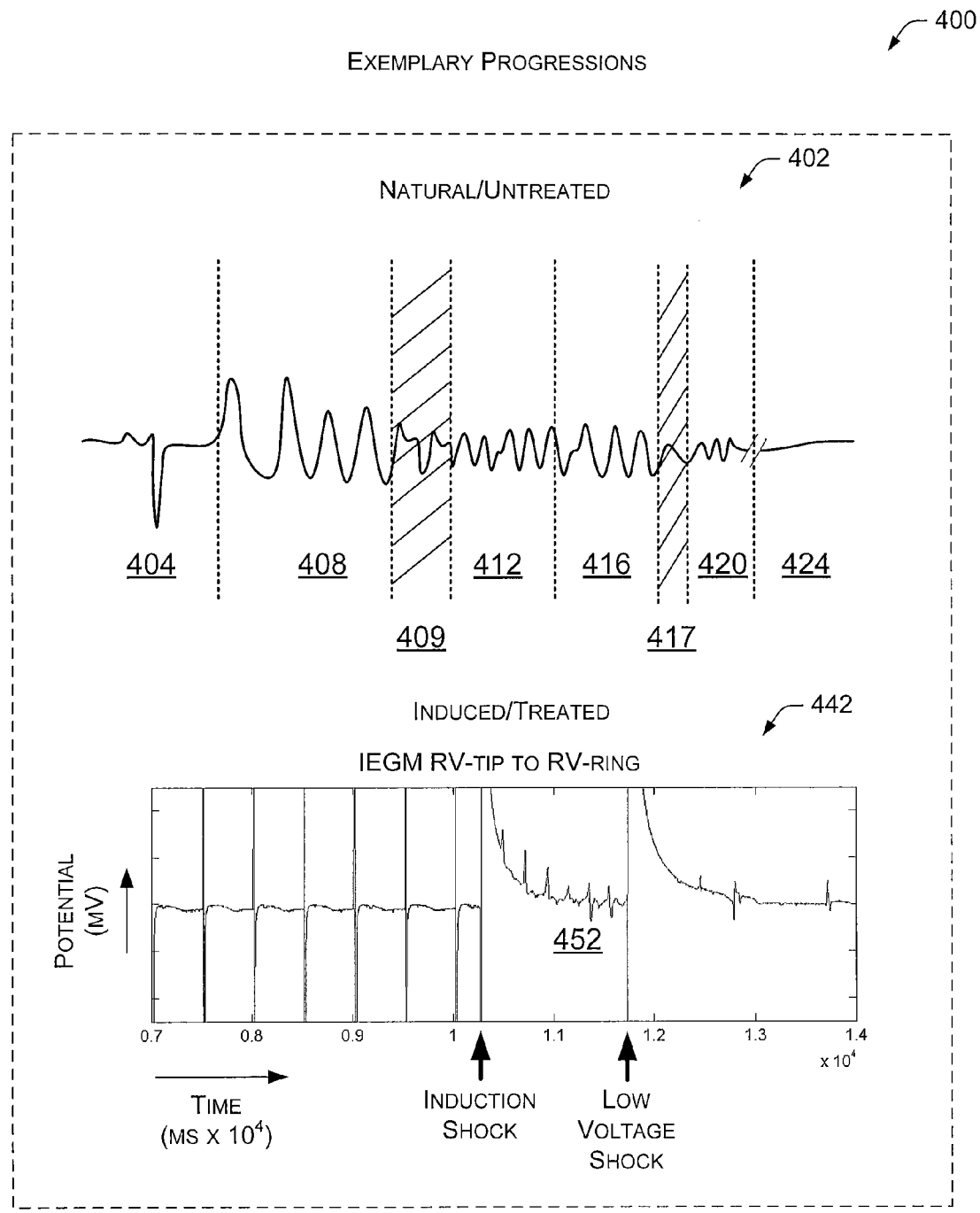
FIG. 4 is a plot of various natural/untreated cardiac waveforms in an exemplary progression of worsening cardiac condition and a plot of various induced/treated cardiac waveforms.

FIG. 4 shows cardiac waveforms of exemplary progressions of worsening cardiac condition 400. The particular progressions shown may vary in form, scale, etc. A first progression 402 represents a natural and untreated progression of worsening cardiac condition that includes arrhythmias (see, e.g., Weiss et al., "Ventricular Fibrillation: How Do We Stop the Waves From Breaking?", *Circ Res.* 2000;87:1103-1107). Various vertical dashed lines separate or designate regions that include a normal sinus region 404 (e.g., one main event), a region 408 of early organized activation having at least some characteristics associated with or indicative of ventricular tachycardia (e.g., about four events), a transition region 409 of more complex morphology and typically a decreased interval that may be associated with or indicative of ventricular fibrillation (VF), an early, coarse ventricular fibrillation (VF) region 412, a later, coarse ventricular fibrillation (VF) region 416 (e.g., may be observed in ischemia induced arrhythmia onset), a coarse to fine ventricular fibrillation (VF) region 417, a fine ventricular fibrillation (VF) region 420 and an asystole region 424.

Figure 12:
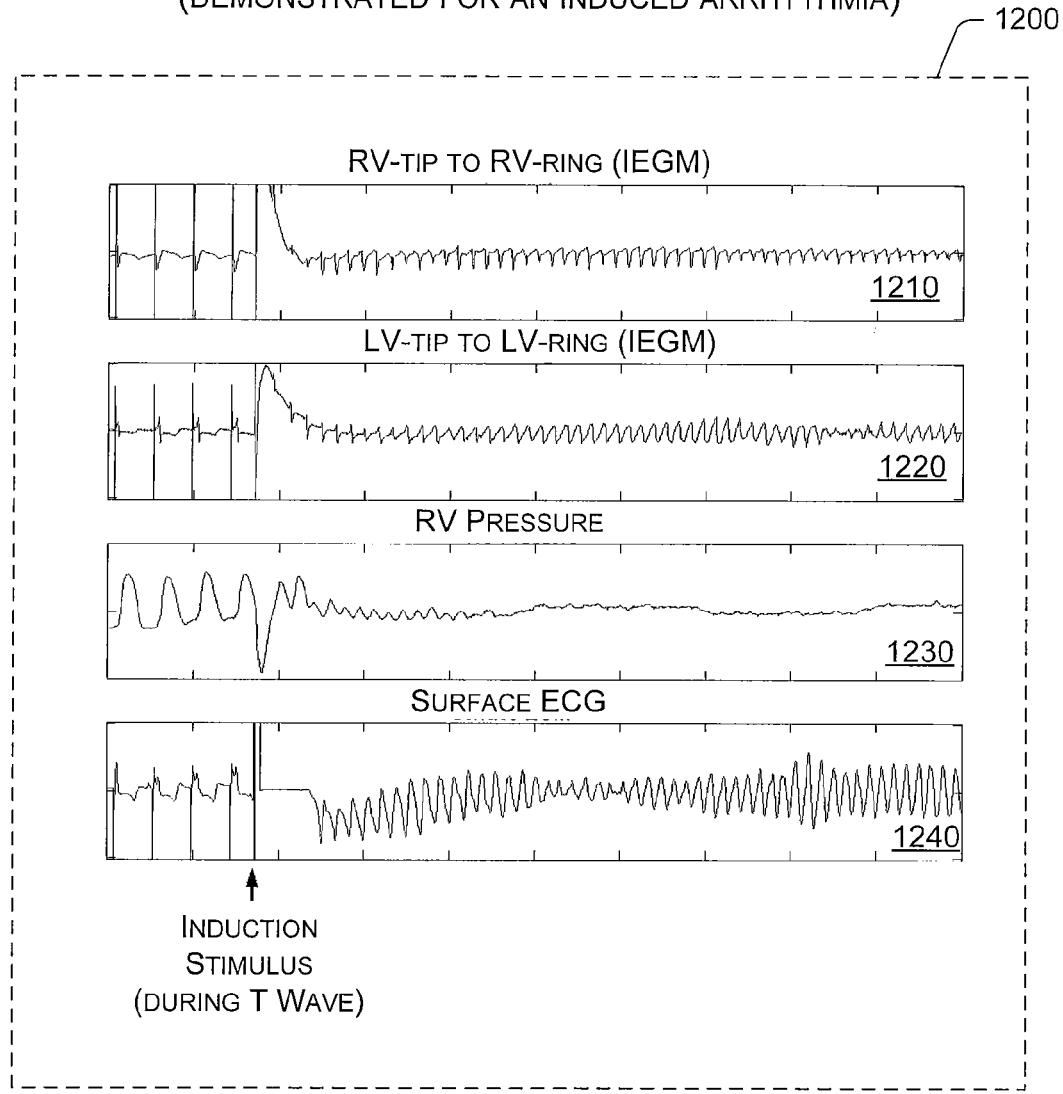
FIG. 12 is a series of plots of IEGMs, blood pressure and ECG for an induced arrhythmia wherein such sensed information may be used in fast arrhythmia detection.

While the exemplary progression 402 is shown with cardiac waveforms of electrical behavior, a similar progression may be noted using other signals. For example, a hemodynamic sensor may detect hemodynamic behavior that indicates compromised cardiac performance. Thus, a hemodynamic sensor may indicate whether a condition is hemodynamically stable or hemodynamically unstable. Such a sensor may be used in conjunction with intracardiac electrograms. Further, intracardiac electrograms, hemodynamic signals, etc., may be analyzed using morphology or other techniques. FIG. 12, described further below, shows various plots of IEGMs and hemodynamic information versus time associated with an induced arrhythmia. FIG. 2, described above, shows an exemplary device that optionally includes one or more physiologic sensors 270, which may include a hemodynamic sensor (e.g., RV pressure sensor, etc.).

A second progression 442 represents an induced and treated progression wherein induction of arrhythmia occurs via a shock administered during a T wave and treatment occurs via an exemplary low voltage shock administered in an arrhythmic region 452. Waveforms in the progression 442 were acquired in a canine trial wherein sensing occurred using a right ventricular tip electrode (see, e.g., the electrode 128 of FIG. 1) and a right ventricular ring electrode (see, e.g., the electrode 130 of FIG. 1). In this example, the region 452 corresponds substantially to the region 408 of early organized activation having at least some characteristics associated with or indicative of ventricular tachycardia and/or the transition region 409 of more complex morphology and typically a decreased interval that may be associated with or indicative of ventricular fibrillation (VF). In this example, delivery of the low voltage treatment shock occurred about 1.5 seconds after the induction shock. In one example, a shock with energy of approximately 1.7 joules and a leading edge voltage of about 180 volts for a biphasic pulse (about 8 ms) was delivered to a load of about 50 ohms to successfully terminate an arrhythmia. An exemplary method includes delivering an early shock (e.g., within a few seconds of indicia of an arrhythmia) with a leading edge voltage of less than approximately 200 volts to terminate an arrhythmia.

Should irregular beats persist, cardiac condition may be classified as ventricular tachycardia (VT), for example, where three irregular beats of ventricular origin exist with a rate in excess of approximately 100 beats per minute. In general, cardiac waveforms appear abnormal for VT and QRS complexes are often difficult to define. VT waveforms may exhibit "notching" and a broad QRS-like segment (e.g., occurring over approximately 120 ms or more). Further, ST segment and T wave typically exhibit opposite polarity compared to a normal QRS. While the sinus node may be depolarizing normally, there is usually complete AV dissociation and P waves may be observed between the QRS-like segments. Ventricular rhythm during VT is somewhat regular and at a rate greater than approximately 100 bpm and generally less than approximately 220 bpm.

A patient may tolerate some degree of VT; however, VT can be associated with life-threatening hemodynamic malfunction. Sometimes, treatment of VT involves drugs such as lidocaine, procainamide, bretylium tosylate, etc. As mentioned above, an implantable device, upon detection of ventricular tachycardia, may act or respond by delivering a cardioversion stimulus. A cardioversion stimulus of an implantable device typically has an energy level less than approximately 10 joules. For example, a study by Bardy et al., "A prospective randomized repeat-crossover comparison of antitachycardia pacing with low-energy cardioversion", *Circulation,* 87:1889-1896 (1993), used up to four therapeutic attempts of low-energy cardioversion beginning with a 0.2 J pulse wherein, if ineffective, pulse energy was increased to 0.4, 1.0, and finally 2.0 J. Of course, an alternative therapy or therapy tier may occur prior to delivery of a cardioversion stimulus. Such alternative therapies may include anti-tachycardia pacing, which typically rely on energy levels that approximate those used in pacing. Various exemplary methods, devices, systems, etc., described herein pertain mainly to defibrillation shock therapy and, in particular, to alternative and/or adjunct shock therapies.

As mentioned in the exemplary progressions 400 of FIG. 4, early, coarse ventricular fibrillation (VF) can follow VT, for example, where VT does not subside or otherwise convert back to a normal sinus rhythm. A transition region typically exists between VT and early, coarse VF, wherein rhythm becomes increasingly irregular and waveforms begin to vary in size and shape. In general, VF is characterized by varying degrees of disorganized depolarization and repolarization of multiple areas within one or both ventricles. Since no significant organized depolarization exists, the ventricles do not contract as a unit. Indeed, gross visual observations during VF often describe the myocardium as quivering. Cardiac output during VF is minimal and inadequate. Of course, an implantable device may detect and possibly record early arrhythmic stages of VT.

As described herein, various exemplary devices, systems and methods aim to terminate VF at the early, coarse stage. For example, an early, coarse stage of VF may be defined by a number of intervals. Upon detection of an early, coarse stage of VF, an implantable device may act or respond by delivering one or more shocks or stimuli to the myocardium. Such early, coarse VF therapy stimuli may be synchronized and/or unsynchronized and typically delivered at energy levels less than those used for conventional ventricular defibrillation. For example, if an early, coarse stage of VF is defined as less than 10 intervals from detection then such stimuli may be delivered during this stage in an effort to terminate VF and convert back to a normal sinus rhythm or even to a less hazardous VT, which may be treated via other pacing and/or stimulation therapies (e.g., anti-tachycardia pacing, cardioversion, etc.). Such early, coarse VF defibrillation therapy may be a sub-tier of a defibrillation therapy tier.

Moving beyond early, coarse VF, after, for example, a certain set number of intervals, VF may be classified as later, coarse VF. Upon detection of an advanced or later, coarse VF, an exemplary implantable device may act or respond by delivering one or more defibrillation stimuli at appropriate energy levels and appropriate times. Such later, coarse VF defibrillation therapy may be a sub-tier of a defibrillation therapy tier.

Moving beyond later, coarse VF, a coarse VF may transition into fine VF. Fine VF is often indicative of an advanced VF, i.e., a VF somewhat removed from a time of onset. As VF becomes finer, treatment can become more difficult with a lessening probability of success. Upon detection of fine VF, an exemplary implantable device may act or respond by delivering one or more defibrillation stimuli at appropriate energy levels and appropriate times. Such fine VF defibrillation therapy may be a sub-tier of a defibrillation therapy tier.

As already mentioned, fine VF may transition to asystole, which may be characterized as a total absence of ventricular electrical activity. Since depolarization does not occur, there is no ventricular contraction. Asystole may occur as a primary event in cardiac arrest, or it may follow VF or pulseless electrical activity (PEA).

If a lower voltage therapy can successfully treat a cardiac condition normally treated via a higher voltage therapy, several advantages may be realized. For example, a lower voltage therapy may result in less pain, an energy savings, and/or less risk or occurrence of block (e.g., AV block, bundle branch block or other block). Further advantages may be gain by early delivery of such therapy as well.

Ventricular asystole can occur also in patients with complete heart block. Detection of asystole may be confused with VF; therefore, a detection technique may use more than one measure to distinguish VF and asystole. In general, treatment for asystole differs from treatment for VF. Fine VF should be treated with defibrillation whereas defibrillation during asystole is potentially harmful. Upon detection of asystole, an exemplary implantable device may inhibit defibrillation therapy and/or trigger or communicate a need to a device, a patient or a care provider (e.g., for administration of a drug, such as epinephrine and/or atropine).

Figure 5:
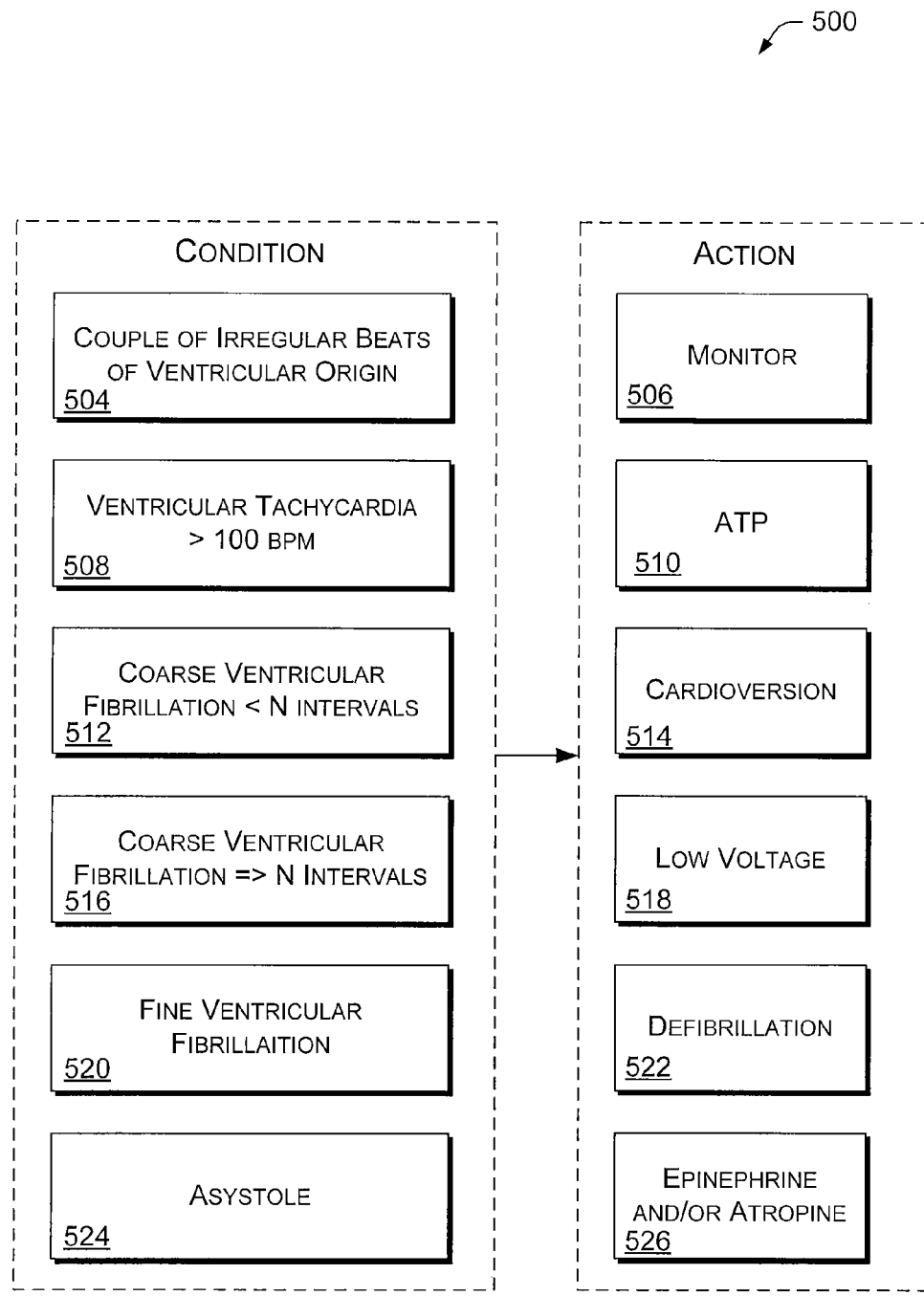
FIG. 5 is a block diagram of various cardiac conditions and actions that an implantable device may take in response to such conditions.

FIG. 5 shows various conditions and actions 500 wherein, for example, an exemplary method may detect a condition and then call for one or more of the actions. The conditions correspond approximately to the progression 402 of FIG. 4. For example, the sinus region 404 may exhibit irregular beats that are unorganized 504, which in turn calls for an action such as increased monitoring 506. Monitoring may include use of an event counter that registers number of irregular beats in a given time or a given number of events. Monitoring may include use of one or more sensors optionally including a hemodynamic sensor (see, e.g., sensors 270 of FIG. 2).

Another condition 508 may arise from irregular beats or may arise independently of a prior detected condition. The condition 508, characterized by ventricular beats having a rate greater than a limit (e.g., 100 bpm), may indicate presence of a ventricular tachycardia. Such a condition may correspond to the region 408 of early organized activation having at least some characteristics associated with or indicative of ventricular tachycardia.

As an alternative or adjunct, cardiac condition may be classified as ventricular tachycardia (VT), for example, where three irregular beats of ventricular origin exist with a rate in excess of a set number of beats per minute. In general, cardiac waveforms appear abnormal for VT and QRS complexes are often difficult to define. VT waveforms may exhibit "notching" and a broad QRS-like segment (e.g., occurring over approximately 120 ms or more). Further, ST segment and T wave typically exhibit opposite polarity compared to a normal QRS. While the sinus node may be depolarizing normally, there is usually complete AV dissociation and P waves may be observed between the QRS-like segments. In general, ventricular rhythm during VT is somewhat regular and typically at a rate greater than approximately 100 bpm and generally less than approximately 220 bpm.

With respect to actions, decision blocks may direct action to one or more branches, for example, a branch corresponding to slow early intervals and a branch corresponding to fast early intervals (e.g., greater than approximately 240 beats per minute). The "fast" branch may proceed to an action such as a low voltage therapy action 514; whereas, the "slow" branch may continue with normal tiered therapy, which may include anti-tachycardia pacing (e.g., action 510), cardioversion (e.g., action 514), etc.

Yet another condition 512 is characterized as coarse ventricular fibrillation of less than a predetermined number of beat or event intervals (e.g., N), for example, representative of an early stage of ventricular fibrillation (VF). As mentioned in the exemplary progression 402 of FIG. 4, early, coarse VF 412 can follow VT, for example, where VT does not subside or otherwise convert back to a normal sinus rhythm. A transition region typically exists between VT and early, coarse VF, wherein rhythm becomes increasingly irregular and waveforms begin to vary in size and shape. In general, VF is characterized by varying degrees of disorganized depolarization and repolarization of multiple areas within one or both ventricles. Since no significant organized depolarization exists, the ventricles do not contract as a unit. Indeed, gross visual observations during VF often describe the myocardium as quivering. Cardiac output during VF is minimal and inadequate. Of course, an implantable device may detect and possibly record early arrhythmic stages of VT.

As described herein, various exemplary devices, systems, methods, etc., aim to terminate VF at the early, coarse stage (e.g., condition 512). For example, an early, coarse stage of VF may be defined by a number of intervals. Upon detection of an early, coarse stage of VF, an implantable device may act or respond by delivering one or more cardioversion level shocks to the myocardium (e.g., action 514). Such shocks may be synchronized and/or unsynchronized and typically delivered at energy levels less than those used for defibrillation. For example, if an early, coarse stage of VF is defined as less than 10 intervals from detection of irregular beats or VT, then such a shock may be delivered during this stage in an effort to terminate VF and convert back to a normal sinus rhythm or even to a less hazardous VT, which may be treated via other pacing and/or stimulation therapies. As already mentioned, a decision block may direct action to one or more branches, as appropriate. Thus, a combination of actions may be implemented in a tiered manner wherein actions are selected from ATP (e.g., action 510), cardioversion (e.g., action 514) and low voltage shock (e.g., action 518).

If the ventricular fibrillation persists, with or without treatment, for a set number of intervals, VF may be classified as later, coarse VF (e.g., condition 516). Upon detection of an advanced or later, coarse VF, an implantable device may act or respond by delivering one or more defibrillation shocks 522 (e.g., optionally as part of a tiered therapy). In general, such shocks are delivered in a synchronized manner, though as to the lack of organized R waves that is typical at this stage in a progression, some uncertainty exists as to benefits of synchronized delivery.

As discussed with respect to the progression 402 of FIG. 4, coarse VF may transition into fine VF, shown in block 520 of FIG. 5. Fine VF is often indicative of an advanced VF, i.e., a VF somewhat removed from a time of onset. As VF becomes finer, treatment can become more difficult with a lessening probability of success. Upon detection of fine VF, an implantable device may act or respond by delivering one or more defibrillation shocks typically at an energy level of approximately 10 joules to approximately 20 joules or more 522 (see, e.g., description of device 100 of FIG. 2 for an even more general range for defibrillation energy of approximately 5 joules to approximately 40 joules). In general, such shocks are delivered in a synchronized manner.

As already mentioned, fine VF may transition to asystole, which may be characterized as a total absence of ventricular electrical activity 524. Since depolarization does not occur, there is no ventricular contraction. Asystole may occur as a primary event in cardiac arrest, or it may follow VF or pulseless electrical activity (PEA).

If a lower voltage therapy can successfully treat a cardiac condition normally treated via a higher voltage therapy, several advantage may be realized. For example, a lower voltage therapy may result in less pain, an energy savings, and/or less risk or occurrence of block (e.g., AV block, bundle branch block or other block).

Ventricular asystole can occur also in patients with complete heart block. Detection of asystole may be confused with VF; therefore, a detection technique may use more than one measure to distinguish VF and asystole. In general, treatment for asystole differs from treatment for VF. Fine VF should be treated with defibrillation whereas defibrillation during asystole is potentially harmful. Upon detection of asystole, an implantable device may trigger or communicate a need for administration of a drug, such as epinephrine and/or atropine 526.

Figure 6:
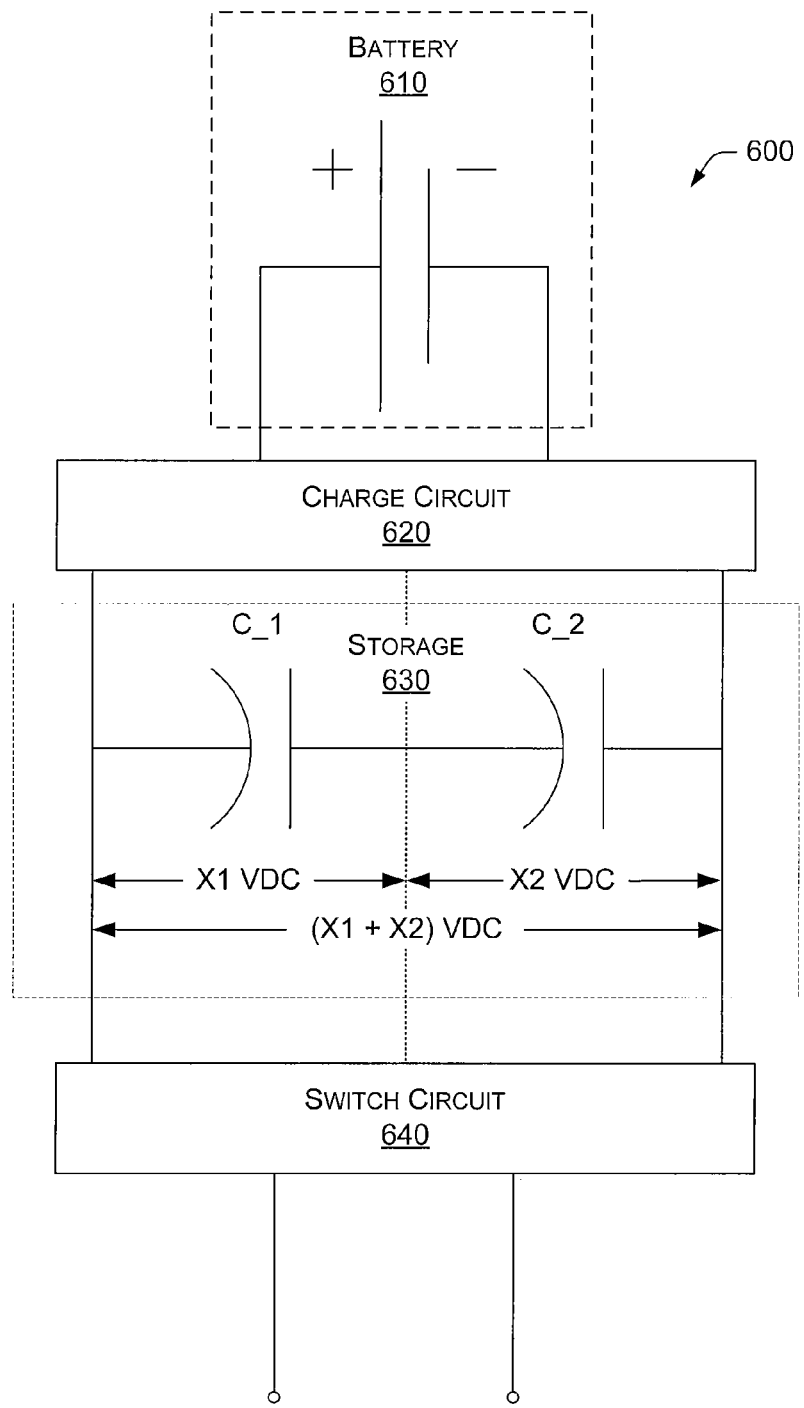
FIG. 6 is an exemplary system for charging and/or discharging a storage that includes capacitors.

FIG. 6 shows an exemplary system 600 for delivering stimulation. The system 600 includes a battery 610, a charge circuit 620, a storage 630 and a switch circuit 640. The battery 610 may be a lithium silver vanadium oxide or other battery, for example, such as the battery 276 of the exemplary device 100 shown in FIG. 2. The charging circuit 620 allows for charging or storing charge in the storage 630. As shown, the storage 630 includes a plurality of capacitors C_1 and C_2. In this example, the capacitors C_1 and C_2 are connectable in series and optionally in parallel and each of the capacitors has an associated voltage, X1 and X2, respectively. Hence, when the capacitors C_1 and C_2 are discharged in series, a total voltage equals approximately the sum of X1 and X2. A switch circuit 640 allows for discharge of at least some of the charge in the storage 630.

Many commercially available implantable defibrillation devices include two capacitors. In such devices, the two capacitors are typically capable of producing approximately 800V when discharged in series. Capacitors for implantable defibrillation devices are often capable of producing a relatively high voltage, have a relatively high capacitance and of relatively small dimensions and hence volume (e.g., two capacitors may occupy about 8 cubic centimeters). For example, at a volumetric storage capacity of about 4.5 J per cubic centimeter, a total charge of about 30 J would require about 7 cubic centimeters. A commercially available implantable defibrillation device may include two 400 volts direct current (VDC), 188 microfarad ($\mu F$) capacitors connected in series to form an equivalent 800 V, 94 $\mu F$ capacitor. This is capable of producing a short pulse of approximately 30 joules and approximately 10 milliseconds in duration.

A normal load is approximately 50 ohms, with a typical minimum requirement of approximately 20 ohms. Many commercially available implantable defibrillation devices can charge two capacitors in approximately 6 to approximately 15 seconds, depending upon the discharge state of the battery. With respect to capacitance, many commercially available implantable defibrillation devices use anode foil having a stored energy density of approximately 4 joules to approximately 5 joules per cubic centimeter. Where suitable, other types (size, material, number, etc.) of capacitors may be used in various exemplary methods, devices, systems, etc. Other types include, but are not limited to, film dielectric capacitors (e.g., PVDF and polycarbonate), which may include extruded film.

Trials performed using a commercially available capacitor demonstrated that an energy charge capable of delivering a shock with a leading edge voltage of about 350 volts could be achieved in about six intervals of a ventricular fibrillation (e.g., less than about 2 seconds). For low voltage shocks with leading edge voltage of about 200 volts, charge time was less than 1 second and typically less than about 700 ms. In general, a stored charge capable of delivering a shock with a leading edge voltage of about 300 volts to a load of about 50 ohms can be achieved using conventional capacitors and charging circuitry in less than 1 second. Tables 1 and 2, shown further below, indicate that a stored charge of about 4 joules and a 300 volt leading edge can be delivered after a charge time of about 0.72 seconds at the beginning of life of a conventional implanted device.

Figure 7:
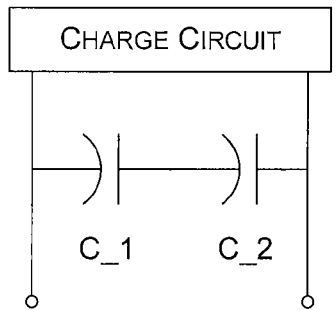
FIG. 7 is a diagram of various exemplary schemes for charging and/or discharging a plurality of capacitors.
Figure 7:
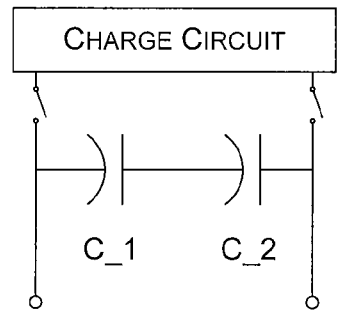
Figure 7:
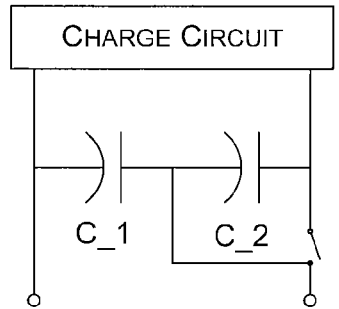
Figure 7:
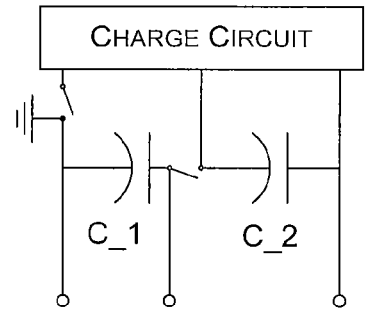

FIG. 7 shows various exemplary schemes 700 for charging and discharging a plurality of capacitors. A scheme 710 allows for discharging capacitors C_1 and C_2 in series and simultaneous charging of the capacitors. A scheme 720 allows for charging of capacitors C_1 and C_2 and separate or isolated discharge of the capacitors, for example, via one or more switches. A scheme 730 allows for discharging capacitor C_1 separately or in isolation from capacitor C_2 while simultaneously allowing for charging of the capacitors. A scheme 740 allows for discharge of capacitor C_1 and simultaneous charging of capacitor C_2. Of course, a variety of variations, arrangements and permutations exist. Such alternatives may be suitable for use in various exemplary methods, systems and/or devices disclosed herein.

Figure 8:
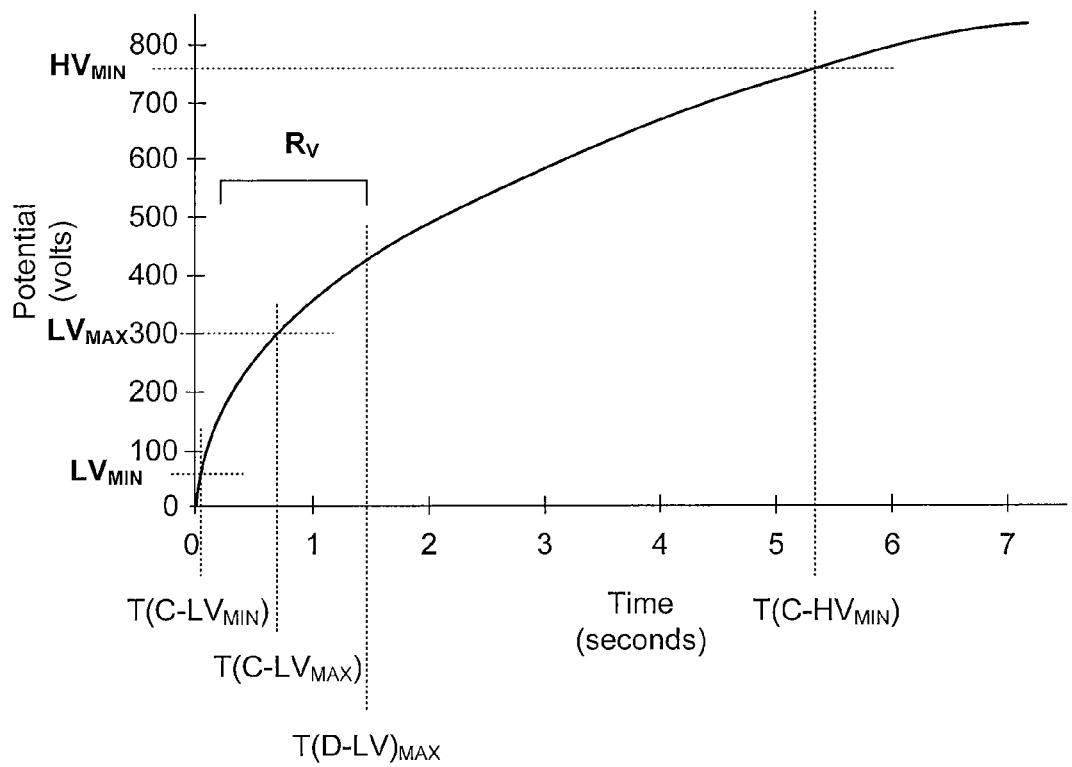
FIG. 8 is a plot of potential versus charge time for a plurality of capacitors.

FIG. 8 shows an exemplary plot 800 of potential in volts versus time in seconds for charging two conventional capacitors such as those described above. The plot 800 includes various exemplary low and high voltage values with corresponding charge times. Tables 1 and 2 include some information related to the plot 800. Table 1 includes potential and charge time information for a charge storage (e.g., capacitors) at beginning of life (BOL) and at time of recommended replacement (ERI). Table 2 includes energy and charge time for a charge storage (e.g., capacitors at beginning of life (BOL) and at time of recommended replacement (ERI). Table 2 includes information for 10 ms by 10 ms (e.g., a biphasic cycle of about 20 ms) decay and for a 65% tilt. Tilt "k" refers to decay in pulse height typically with respect to a frequency "f" of discharge and/or a pulse length "tp". For example, the following equation (Eqn. 1) may represent tilt:

$$k = \Delta V/V_0 = 0.5*(1-e^{-tp/RC}) \quad (1)$$

where tp=0.5/f and $\Delta V$ corresponds to a decrease in voltage over the time tp and $V_0$ corresponds to an initial voltage.

TABLE 1

Charge Voltage and Charge Time

| Potential (V) | Time-BOL(s) | Time-ERI(s) |
|---|---|---|
| 0 | 0.00 | 0.00 |
| 50 | 0.01 | 0.00 |
| 100 | 0.07 | 0.09 |
| 150 | 0.18 | 0.26 |
| 200 | 0.32 | 0.49 |
| 250 | 0.50 | 0.77 |
| 300 | 0.72 | 1.11 |
| 350 | 0.98 | 1.53 |
| 400 | 1.30 | 2.04 |
| 450 | 1.67 | 2.65 |
| 500 | 2.10 | 3.37 |
| 550 | 2.59 | 4.18 |
| 600 | 3.15 | 5.10 |
| 650 | 3.77 | 6.13 |
| 700 | 4.47 | 7.29 |
| 750 | 5.27 | 8.64 |
| 775 | 5.72 | 9.41 |
| 800 | 6.21 | 10.27 |
| 815 | 6.53 | 10.83 |
| 830 | 6.86 | 11.43 |

TABLE 2

Charge Time and Delivered Energy

| | 10 ms/10 ms | | 65% Tilt | |
|---|---|---|---|---|
| Energy (J) | Time-BOL(s) | Time-ERI(s) | Time-BOL(s) | Time-ERI(s) |
| 0 | 0.00 | 0.00 | 0.00 | 0.00 |
| 2 | 0.36 | 0.55 | 0.36 | 0.00 |
| 4 | 0.72 | 1.10 | 0.71 | 0.54 |
| 6 | 1.08 | 1.68 | 1.08 | 1.09 |
| 8 | 1.47 | 2.30 | 1.45 | 1.66 |
| 10 | 1.86 | 2.96 | 1.85 | 2.27 |
| 12 | 2.27 | 3.64 | 2.25 | 2.91 |
| 14 | 2.69 | 4.34 | 2.68 | 3.57 |
| 16 | 3.13 | 5.06 | 3.11 | 4.25 |
| 18 | 3.57 | 5.78 | 3.55 | 4.94 |
| 20 | 4.03 | 6.53 | 4.00 | 5.65 |
| 22 | 4.50 | 7.31 | 4.47 | 6.39 |
| 24 | 4.98 | 8.14 | 4.95 | 7.14 |
| 25 | 5.23 | 8.57 | 5.20 | 7.94 |
| 26 | 5.49 | 9.02 | 5.46 | 7.94 |
| 27 | 5.76 | 9.48 | 5.73 | 8.35 |
| 28 | 6.03 | 9.95 | 6.00 | 8.77 |
| 29 | 6.32 | 10.43 | 6.28 | 9.21 |
| 30 | 6.62 | 10.90 | 6.58 | 9.67 |
| 31 | 6.95 | 11.35 | 6.88 | 10.61 |

The plot 800 also includes a voltage divider bracket "$R_V$" which represents use of a voltage divider to allow for delivery of a reduced voltage where the potential exceeds a maximum low voltage value "$LV_{max}$". The plot 800 shows a corresponding time "$T(D-LV_{max})$", which may be a maximum time wherein a voltage divider may be applied. In general, such a voltage divider aims to produce a reduced voltage of at least a minimum low voltage "$LV_{min}$". During operation, the maximum low voltage $LV_{max}$ is achieved at a time "$T(C-LV_{max})$" and the minimum low voltage $LV_{min}$ is achieved at a time "$T(C-LV_{max})$". The plot 800 includes a minimum high voltage "$HV_{min}$" and a corresponding time "$T(C-HV_{min})$".

Figure 9:
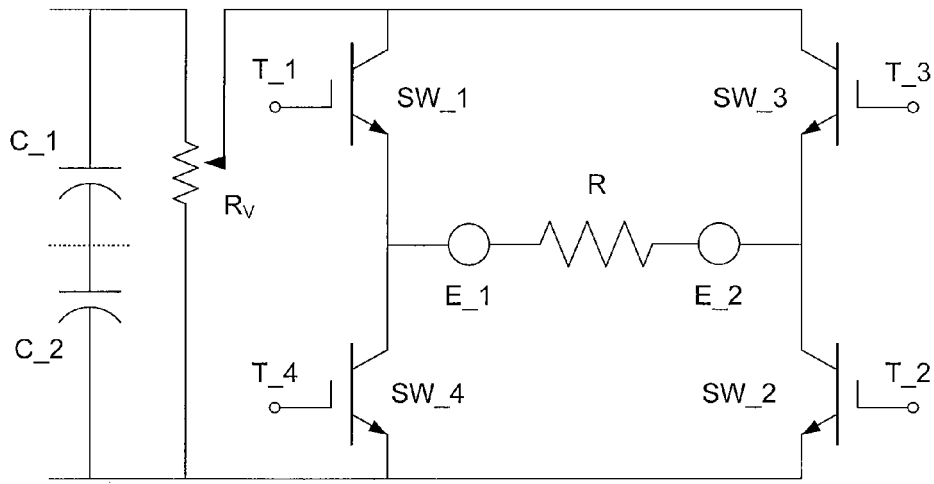
FIG. 9 is a diagram of an exemplary circuit that includes an H-bridge and a performance plot of such a circuit.
Figure 9:
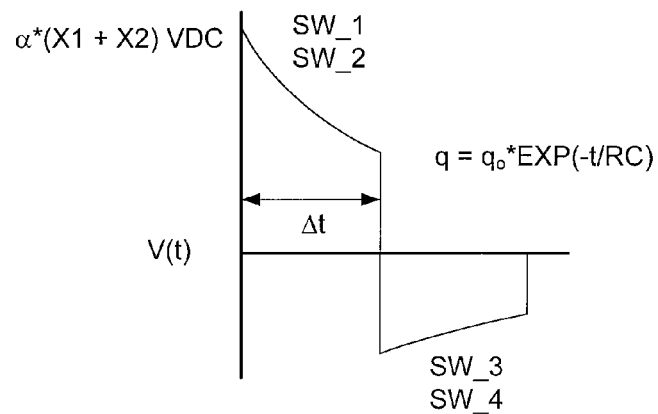

FIG. 9 shows an exemplary circuit 900 that includes a switchable H-bridge 910 connected to two capacitors, C_1 and C_2 and a corresponding discharge curve 920. The exemplary circuit 900 optionally includes a voltage divider $R_V$ which may be controlled via software and/or hardware and capable of reducing voltage to a desired value. The plot of the discharge curve 920 indicates that the voltage divider may reduce leading edge voltage by a factor α, where α is less than or equal to 1.

In this example, the H-bridge 910 includes four insulated gate bipolar transistors (IGBTs) labeled SW_1, SW_2, SW_3 and SW_4. Of course, other types of switches may be used in addition to or as alternatives to the IGBT switches and/or other switch configurations may be used. In the switchable H-bridge 910, the switches SW_1, SW_2, SW_3 and SW_4 may be triggered by timing signals received at trigger points labeled T_1, T_2; T_3 and T_4, respectively. The H-bridge includes two electrodes labeled E_1 and E_2, which have a load labeled R, which may represent a patient (e.g., a portion of myocardium, other tissue, etc.). Thus, control of the switches via the trigger points may control discharge of the capacitors labeled C_1 and C_2 across the load R.

Various exemplary circuits allow for simultaneous charge and discharge and/or switching that allows for pseudo-simultaneous charge and discharge (e.g., alternating, etc.). In general, normal charging of the capacitors C_1 and C_2 follows behavior exhibited in the plot 800 of FIG. 8.

Biphasic discharge pulses have proven quite effective in various commercially available implantable defibrillation devices. For example, studies conducted on implantable defibrillation devices have shown that biphasic discharge pulses result in a lower defibrillation threshold when compared to monophasic discharge pulses.

Capacitors typically discharge in a manner that can be suitably modeled by an equation including an exponential decay term. For example, the following equation is used commonly to determine charge with respect to time during discharge:

$$q(t) = q_0 e^{-t/RC}$$

where q(t), represents charge with respect to time, $q_0$, represents charge at an initial time, R is a resistance or load and C is capacitance (e.g., an RC circuit).

While biphasic pulses have proven useful, other phase pulses are possible and may be used where suitable. For example, the exemplary discharge plot 920 shows voltage (or charge) with respect to time for various switch positions. Upon discharge, switches SW_1 and SW_2 are open while SW_3 and SW_4 are closed for a duration Δt (also see, e.g., tp). The duration Δt may be on the order of approximately 2 ms to approximately 4 ms or other suitable time and may be adjustable to suit a particular need. A traditional biphasic pulse may consist of switching switches SW_1 and SW_2 from open to closed while switching switches SW_3 and SW_4 from closed to open (either simultaneously or with a delay). Such a biphasic pulse is often referred to as a truncated biphasic exponential (TBE). Discharge may continue for a time $t_d$, which represents the time at which substantially all of the charge of the capacitors C_1 and C_2 has been discharged (e.g., approximately 99% of $q_0$, etc.). In this example, the capacitors C_1 and C_2 discharge in series.

Figure 10:
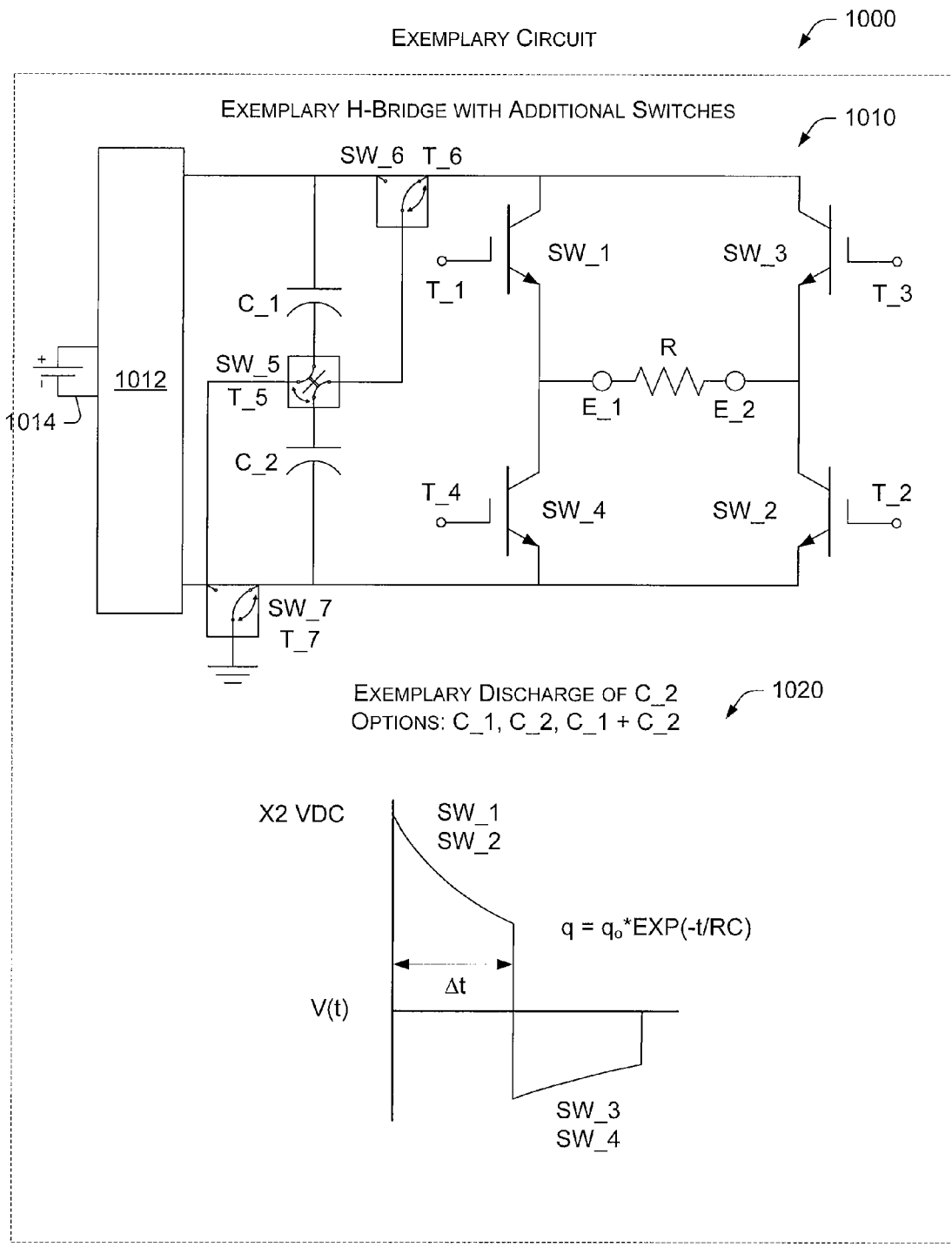
FIG. 10 is a diagram of an exemplary circuit that includes an H-bridge and additional switches and a performance plot of such a circuit.

FIG. 10 shows an exemplary circuit 1000 that includes a switchable H-bridge 1010 connected to two capacitors, C_1 and C_2 and a charge circuit 1012 and a corresponding discharge curve 1020. The charge circuit 1012 is further connected to a battery 1014. The exemplary circuit 1000 optionally includes a voltage divider $R_V$ which may be controlled via software and/or hardware and capable of reducing voltage to a desired value.

In this example, the H-bridge 1010 includes four insulated gate bipolar transistors (IGBTs) labeled SW_1, SW_2, SW_3 and SW_4 and additional switches labeled SW_5, SW_6 and SW_7, which optionally rely on IGBTs and/or other switching technology. In the switchable H-bridge 1010, the switches SW_1, SW_2, SW_3 and SW_4 may be triggered by timing signals received at trigger points labeled T_1, T_2, T_3 and T_4, respectively, while the switches SW_5, SW_6 and SW_7 may be triggered by timing signals received at corresponding trigger points labeled T_5, T_6 and T_7, respectively. The H-bridge includes two electrodes labeled E_1 and E_2, which have a load labeled R, which may represent a patient (e.g., a portion of myocardium, other tissue, etc.). Thus, control of the switches via the trigger points may control discharge of the capacitors labeled C_1 and/or C_2 across the load R. Further, control of the switches SW_5, SW_6 and SW_7 can allow for selective charging of one capacitor (e.g., C_1) and selective discharging of another capacitor (e.g., C_2).

The switch SW_5 allows for isolating the capacitors C_1 and C_2 and for connecting an electrode of one capacitor with an opposite electrode of the other capacitor, for example, to allow for a connecting the capacitors in series. The switch SW_6 allows for isolating the capacitors C_1 and C_2 and, in combination with switches SW_5 and SW_7, the capacitor C_2 can be isolated from the capacitor C_1 and the charge circuit 1012. As shown, the switch SW_7 allows for isolating the capacitor C_2 and the H-bridge from the charge circuit 1012, for example, by switching to a ground, which may be common with the ground of the battery 1014 and/or which may serve as a ground for the charge circuit 1012.

In the example 1010, the various switches may be implemented without changes to the charge circuit 1012. In an alternative example, a charge circuit may include modifications as appropriate.

The exemplary discharge plot 1020 shows discharge of the capacitor C_2 with respect to time. In this example, the voltage or charge at an initial time is equal to that of the capacitor C_2 alone (e.g., leading edge voltage of approximately X2 VDC). Thus, the capacitor C_2 can discharge while the capacitor C_1 charges. As explained with respect to FIG. 7, the exemplary circuit 1000 has some features of the exemplary scheme 740, which allows for discharge of one capacitor and simultaneous charging of another capacitor through use of a plurality of switches.

The exemplary circuit 1000 also allows for switching between discharge of the capacitor C_2 and discharge of the capacitors C_1 and C_2 in series across the load R. As described herein, such control can allow for delivery of one or more low voltage stimulation pulses that aim to terminate or convert early, coarse ventricular fibrillation. In the instance that such action is unsuccessful, the exemplary circuit 1000 allows for discharge of one or more higher voltage, defibrillation pulses (e.g., TBE, etc.). Time is often of the essence in treatment of ventricular fibrillation and the exemplary circuit 1000 allows for several charge and discharge schemes with different time characteristics, such as, charge time, discharge time, etc. The exemplary circuit 1000 optionally includes a voltage divider, which may be software and/or hardware controlled.

Figure 11:
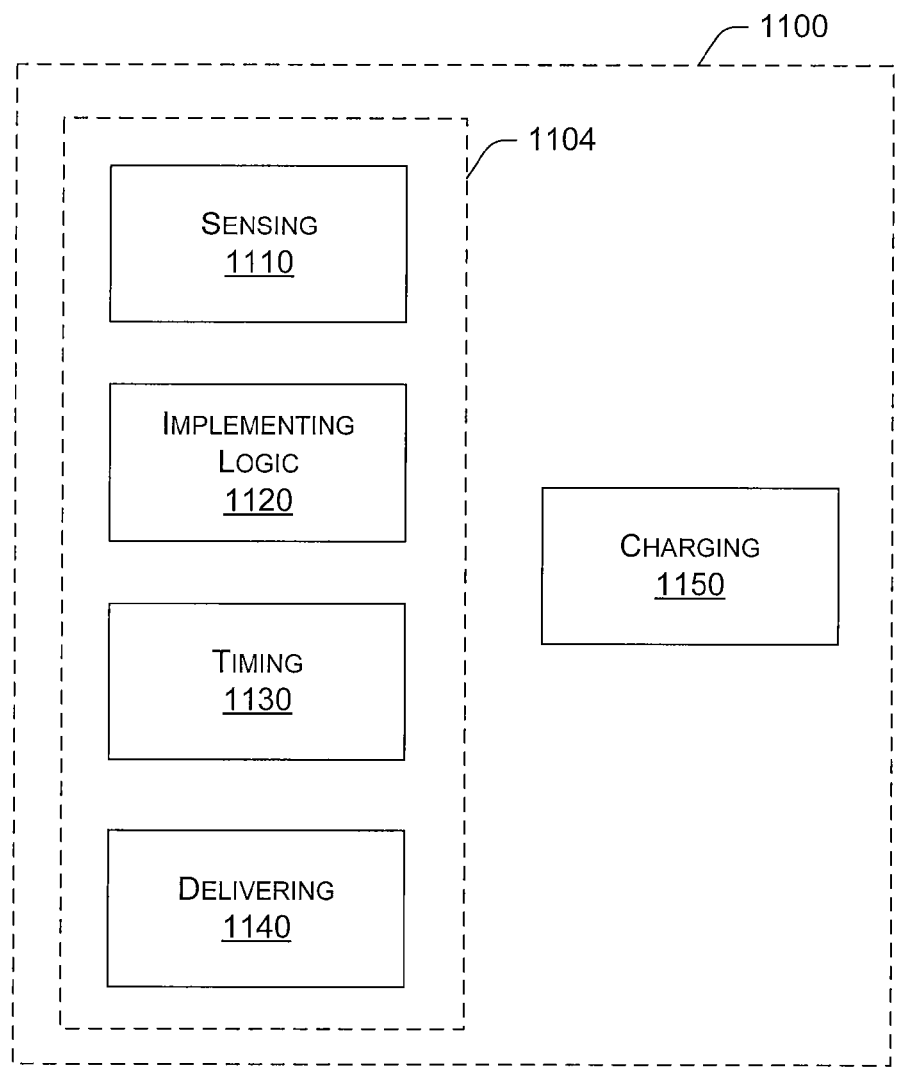
FIG. 11 is a block diagram of an exemplary device capable of sensing cardiac conditions, implementing control logic, timing one or more switches, delivering a charge and charging a charge storage.

FIG. 11 shows a block diagram of various components of an exemplary implantable stimulation device 1100 that can perform various functions. The components may relate to components of the exemplary device 100 of FIGS. 1 and 2. Further, the components may include hardware and/or software. The components in the block 1104 include a sensing block 1110, an implementing logic block 1120, a timing block 1130 and a delivering block 1140. These blocks may be used to determine if and when an early low voltage pulse should be delivered. For example, the sensing block 1110 may sense a cardiac condition indicative of ventricular tachycardia and/or early ventricular fibrillation. The sensed information related to the cardiac condition may be used in the implementing logic block 1120 that can implement logic to determine appropriate control parameters. The timing block 1130 may use the control parameters to implement appropriate control, for example, by transmitting timing signals to appropriate switches, etc. The delivering block 1140 can then deliver the early low voltage pulse accordingly, in an effort to terminate or convert the early stage ventricular fibrillation. A charging block 1150 may participate actively in the process outlined above or it may simply charge one or more capacitors (or other charge storage) without regard to implementation of such an early ventricular defibrillation termination or conversion method.

FIG. 12 shows various exemplary plots 1200 of sensed information versus time for an induced arrhythmia, which is labeled as a stimulus delivered during a T wave. The various sensed information may correspond to a physiological sensor (s) 270 as shown in FIG. 2 and described above. The plot 1210 includes sensed information using a RV-tip electrode and an RV-ring electrode. The plot 1210 indicates that this information is optionally suitable for fast detection of an arrhythmia. The plot 1220 includes sensed information using a LV-tip electrode and a LV-ring electrode. The plot 1220 indicates that this information is optionally suitable for fast detection of an arrhythmia. The plot 1230 includes sensed information using a pressure sensor to sense right ventricular pressure "RV Pressure". The plot 1230 indicates that this information is optionally suitable for fast detection of an arrhythmia. The plot 1240 includes sensed information using surface ECG electrodes. This plot 1240 indicates that this information is optionally suitable for fast detection of an arrhythmia.

The information in the plots 1200 includes information related to hemodynamic condition indicative of ventricular fibrillation. For example, the information of the plot 1230 is related to blood pressure in the right ventricle wherein a decrease in blood pressure is a hemodynamic condition indicative of ventricular fibrillation. In this specific example, a decrease in blood pressure for a period greater than approximately 0.5 second to approximately 1 second may be indicative of ventricular fibrillation. Information from other parts of the arterial system may also be used as indicators of ventricular fibrillation and may be suitable for fast detection.

Various exemplary methods, devices, systems, etc., described herein optionally allow for charging during discharging. For example an exemplary device optionally operates a charging circuit and an output stage or delivery circuit (H-Bridge) simultaneously. According to such a device, fast detection may occur of a cardiac condition (e.g., ventricular fibrillation and/or a precursor thereto, etc.) which, in turn, causes a charger circuit turns on and remains on while an "early therapy" of one or more low energy stimuli or shocks are delivered. Sensing of cardiac condition may continue wherein the charger circuit is remains on and the device decides whether a conversion to sinus rhythm has occurred. Upon such an occurrence, the exemplary device may turn off the charger circuit. However, if conversion did not occur, the condition did not improve, and/or the condition worsened, then charging continues, as appropriate, to increase stored energy to a level suitable for high voltage therapy. For example, such an exemplary device may discontinue charging upon achieving a desired charge and then command an output stage to deliver conventional high voltage therapy (e.g., delivery of a defibrillation shock of approximately 800 V).

Figure 13:
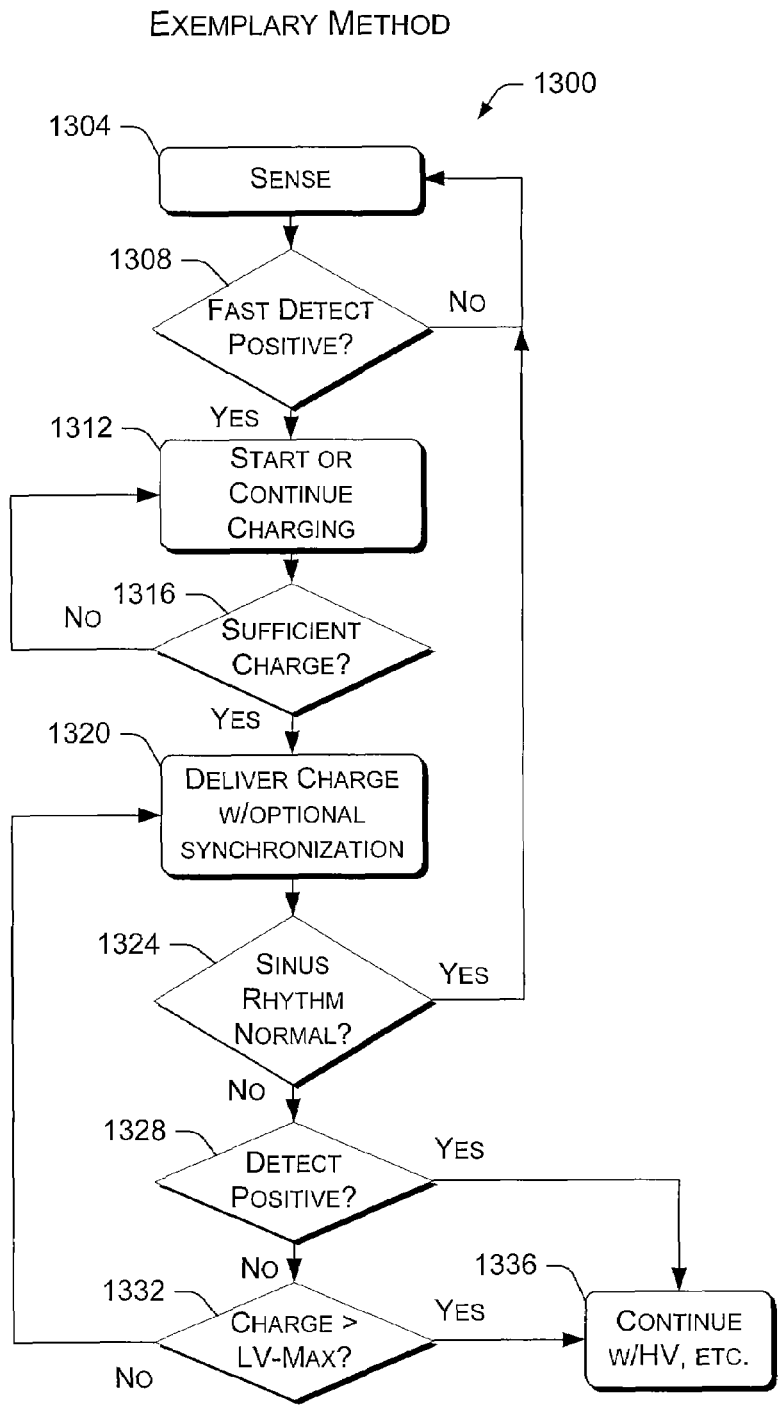
FIG. 13 is a block diagram of an exemplary method for delivering a charge to the myocardium to terminate or convert an arrhythmia.

FIG. 13 shows a block diagram of an exemplary method 1300 for delivering a charge to the myocardium to terminate or convert an arrhythmia. Such an exemplary method optionally allows for charging during discharging. The exemplary method 1300 commences in a sense block 1304 that senses information germane to cardiac performance. A fast detect decision block 1308 uses such information and/or other information to decide or determine whether any type of arrhythmia exists, for example, whether VT, a VT transition to VF, or early VF exist. If no arrhythmias exist, or relevant precursors thereto, then the method 1300 continues in the sense block 1304. However, if the decision block 1308 decides that an arrhythmic condition exists or an onset of such a condition is likely to occur (e.g., according to a probability determination, etc.), then the method 1300 continues in a charge block 1312 wherein charging commences or, if already in progress, charging continues. In general, the charging block 1312 aims to charge one or more capacitors, as appropriate (see, e.g., various examples above).

During charging or optionally during a break in charging, a charge level decision block 1316 decides whether the one or more capacitors have a charge level sufficient for purposes of terminating or converting a present arrhythmic condition or precursor thereto. If the decision block 1316 decides or determines that the charge accumulated by the one or more capacitors is insufficient, then the method 1300 continues charging at the charge block 1312; otherwise, the method 1300 continues at a delivery block 1320. If a situation arises where stored charge or stored charge at a delivery time exceeds a desired energy, then a voltage divider or other reduction technique may act to deliver less than all of the stored charge or to deliver charge from less than all capacitors of a charge storage (e.g., for charge storages that include more than one capacitor). FIG. 9 includes a voltage divider (e.g., resistance $R_V$), which can alter a parameter $\alpha$ for control of a leading edge voltage based on charge stored in capacitors C_1 and C_2. Such an arrangement is optionally implemented in the exemplary circuit 1010 of FIG. 10 or other circuits.

The delivery block 1320 delivers a charge to the myocardium in an effort to terminate or convert an arrhythmic condition or a potentially arrhythmic condition. The delivery block 1320 may deliver the charge via one or more leads and/or via two or more electrodes. Various studies indicate that early stages of ventricular fibrillation may be terminated by one or more stimuli or shocks delivered to or near the septum between the right and left ventricles. A goal of such stimuli or shocks may be to prevent or halt breakup of reentry wavefronts.

As discussed with respect to the exemplary progression 400 of FIG. 4, breakup can worsen cardiac condition. In general, delivered stimuli should aim to prevent breakup of wavefronts that propagate along the septum because the septum is typically an important path for conduction of normal sinus wavefronts. For example, as wavefronts breakup (e.g., into "wavelets"), heterogeneity of tissue depolarization and/or repolarization increases, which, in turn, decreases the chance of a normal sinus wavefront controlling ventricular contraction. Hence, in one example, an electrode is positioned in a patient's right ventricle and proximate to the septum.

Other examples include use of conventional defibrillation leads and electrodes. Various electrode arrangements include RV-coil electrode to a can electrode and/or an electrode in the superior vena cava; and an additional left ventricular electrode-bearing lead implanted via the coronary sinus, which may be beneficial if a dominant early wavefront exists in the left ventricle.

After delivery of the one or more stimuli, the method 1300 continues in a sinus rhythm decision block 1324, which decides or determines, for example, after a sufficient delay, whether a normal sinus rhythm exists. If the decision block 1324 decides that a normal sinus rhythm exists, then the delivery was successful at terminating the particular cardiac condition and the method 1300 continues, for example, at the sense block 1304. However, if the decision block 1324 decides that a normal sinus rhythm does not exist, then the method 1300 continues at another decision block 1328.

The decision block 1328 decides or determines on the basis of sensed and/or other information whether a potentially life-threatening cardiac condition exists. If such a condition exists, then the method 1300 continues in an alternative therapy block 1336, which may delivery one or more higher voltage stimuli or shocks or take other action. If the decision block 1328 decides that such a cardiac condition does not exist, then the method 1300 continues at yet another decision block 1332 that decides or determines whether the charge on the one or more capacitors is greater than a maximum value suitable for a low voltage stimulation therapy. If the decision block 1332 decides that the charge exceeds some limit, then the method 1300 continues by progressing to the alternative therapy block 1336, which may simply return to the sense block 1304, etc. However, if the charge is less than some prescribed limit, then the method 1300 may return to the delivery block 1320 and deliver the charge to the myocardium in a prophylactic effort that reduces the chance of reinitiation of the treated cardiac condition.

Figure 14:
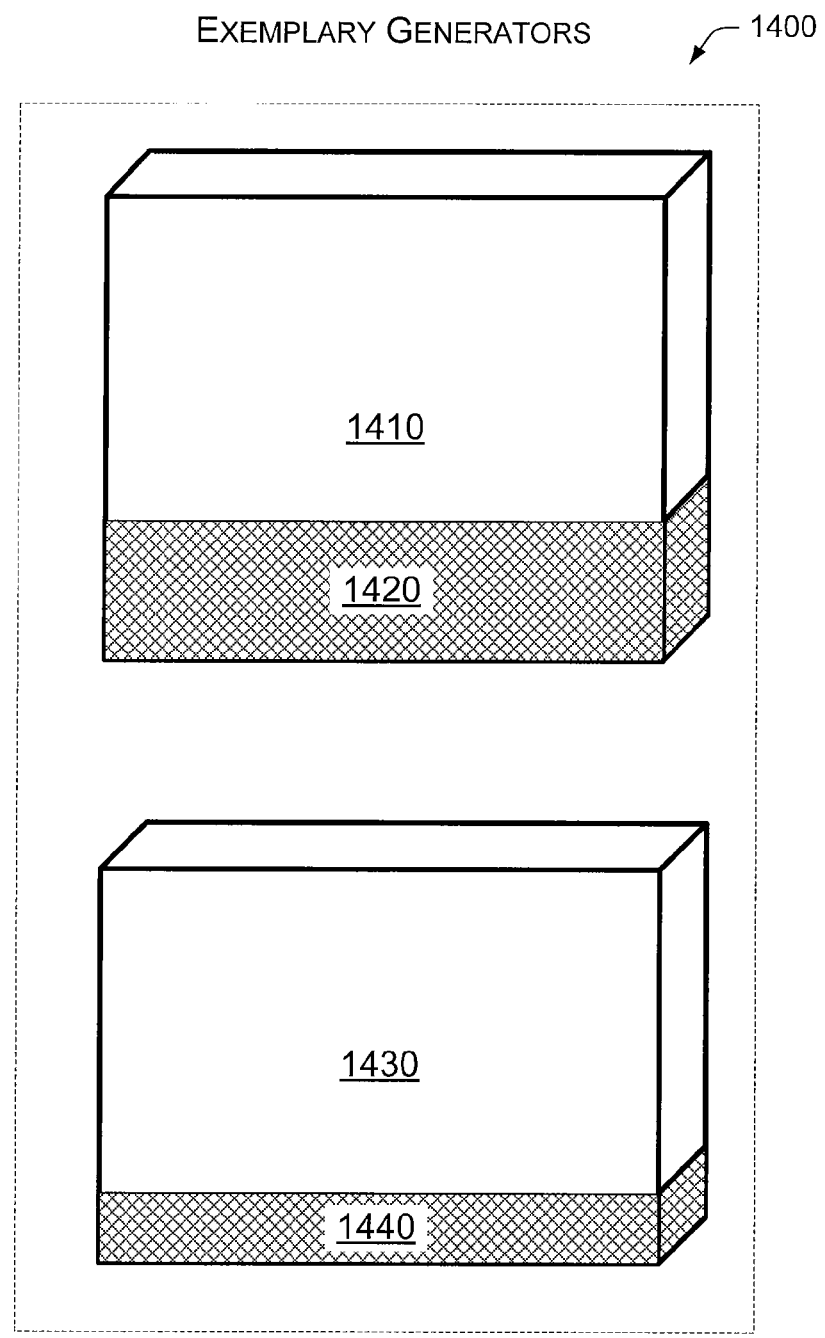
FIG. 14 is a schematic diagram of two exemplary devices having one or more capacitors.

In instances where low voltage therapy proves successful, an opportunity exists for use of a smaller implantable device. FIG. 14 shows a schematic diagram of two exemplary devices having one or more capacitors. As already mentioned, conventional implantable defibrillation devices typically include two capacitors that account for approximately 20% to approximately 30% of the total volume of an implanted defibrillation device. The schematic diagram 1400 includes an exemplary device 1410 having a capacitor section 1420 that occupies about 30% of the device volume and another exemplary device 1430 having a capacitor section 1440 that occupies about 15% of the device volume. Therefore, an exemplary device capable of successfully treating early ventricular fibrillation has a volume proportionately less than that of a conventional implantable defibrillation device that relies on one or more capacitors to produce defibrillation stimuli of approximately 800 volts. Such an exemplary device optionally relies on one capacitor capable of producing stimuli or shocks of approximately 400 volts or less wherein such stimuli or shocks can successful treat early stages of ventricular fibrillation. In an alternative, an exemplary device may include two capacitors that could achieve a stored charge sufficient to deliver a shock with a leading edge voltage of about 800 volts (e.g., about 50 ohm load) wherein source capacitance is reduced (e.g., $(C\_1*C\_2)/(C\_1 + C\_2)$).

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
   detecting an arrhythmic condition;
   in response to the detecting, delivering a low voltage cardiac stimulus using at least one partially charged capacitor within approximately 2 seconds of an initial detection of the arrhythmic condition;
   determining whether the low voltage cardiac stimulus terminated the arrhythmic condition; and
   delivering a higher voltage cardiac stimulus if the low voltage cardiac stimulus did not terminate the arrhythmic condition.

2. The method of claim 1 wherein detecting an arrhythmic condition comprises detecting a predetermined number of events.

3. The method of claim 1 further comprising, in response to the detection, charging a capacitor for a period of time that corresponds to a predetermined number of events.

4. The method of claim 1 wherein delivering a low voltage cardiac stimulus comprises delivering the low voltage cardiac stimulus within a predetermined number of events.

5. The method of claim 2 wherein the events comprise intervals.

6. The method of claim 1, wherein the detecting detects a hemodynamic condition indicative of the arrhythmic condition.

7. The method of claim 6, wherein the hemodynamic condition comprises a decrease in blood pressure associated with the right ventricle.

8. The method of claim 1, wherein the detecting detects onset of ventricular fibrillation.

9. The method of claim 8, wherein the delivering the low voltage cardiac stimulus occurs within approximately 10 intervals from the detected onset of ventricular fibrillation.

10. The method of claim 8, wherein the ventricular fibrillation comprises early, coarse ventricular fibrillation.

11. The method of claim 1, wherein the delivering the low voltage cardiac stimulus includes discharging one or more capacitors and further comprising charging one or more other capacitors during the delivering.

12. The method of claim 1, wherein an H-bridge allows for the delivering of the low voltage cardiac stimulus.

13. The method of claim 12, wherein the H-bridge further allows for the delivering of the higher voltage cardiac stimulus.

14. A method comprising:
    detecting coarse ventricular fibrillation;
    delivering a low voltage cardiac stimulus using at least one partially charged capacitor within approximately 10 intervals from the detected onset of the early, coarse ventricular fibrillation;
    determining whether the low voltage cardiac stimulus terminated the ventricular fibrillation; and
    delivering a higher voltage cardiac stimulus if the low voltage cardiac stimulus did not terminate the arrhythmic condition.

15. The method of claim 14, wherein the delivering the low voltage cardiac stimulus includes discharging one or more capacitors and further comprising charging one or more other capacitors during the delivering.

16. The method of claim 15, wherein an H-bridge allows for the delivering of the low voltage cardiac stimulus.

17. The method of claim 16, wherein the H-bridge further allows for the delivering of the higher voltage cardiac stimulus.

18. A device comprising:
    means for detecting an arrhythmic condition;
    in response to the detecting, means for delivering a low voltage cardiac stimulus using at least one partially charged capacitor within approximately 2 seconds of an initial detection of the arrhythmic condition;
    means for determining whether the low voltage cardiac stimulus terminated the arrhythmic condition; and
    means for delivering a higher voltage cardiac stimulus if the low voltage cardiac stimulus did not terminate the arrhythmic condition.

19. The device of claim 18, wherein the device further comprises a battery and one or more capacitors for storing charge.

20. The device of claim 18, wherein the means for delivering the low voltage cardiac stimulus includes one or more switches configurable to discharge one or more capacitors via two or more electrodes.

* * * * *

UNITED STATES PATENT AND TRADEMARK OFFICE
CERTIFICATE OF CORRECTION

PATENT NO. : 7,660,629 B2  
APPLICATION NO. : 11/564725  
DATED : February 9, 2010  
INVENTOR(S) : Province et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 695 days.

Signed and Sealed this

Thirtieth Day of November, 2010

David J. Kappos
*Director of the United States Patent and Trademark Office*